United States Patent [19]

Lewis et al.

[11] Patent Number: 5,182,402
[45] Date of Patent: Jan. 26, 1993

[54] HERBICIDAL COMPOSITIONS

[75] Inventors: Terence Lewis, Quintilis; Harjinder S. Bansal, Chisbury; Raymond L. Sundley, Mallard; Michael R. Bartley, Lyme Regis; Walter Hepworth, Macclesfield; David J. Gilman, Crowthorne; Ian T. Kay, Mousehole; David J. Collins, Wokingham, all of Great Britain

[73] Assignee: Imperial Chemical Industries PLC, London, England

[21] Appl. No.: 763,035

[22] Filed: Sep. 19, 1991

Related U.S. Application Data

[62] Division of Ser. No. 432,104, Nov. 2, 1989, Pat. No. 5,084,083.

[51] Int. Cl.$^5$ .......................... C07D 277/30
[52] U.S. Cl. .................. 548/204; 548/187; 548/193
[58] Field of Search .............. 548/204, 193, 187

[56] References Cited

U.S. PATENT DOCUMENTS

| | | | |
|---|---|---|---|
| 3,418,331 | 12/1968 | Yates et al. | 71/90 |
| 3,694,450 | 9/1972 | Wei | 71/90 |
| 3,749,787 | 7/1973 | Hepworth et al. | 71/90 |
| 3,787,433 | 1/1974 | Wei | 71/90 |
| 3,803,161 | 4/1974 | Wei | 71/90 |
| 3,859,280 | 1/1975 | Wei | 71/90 |
| 4,243,407 | 1/1981 | Cahoy | 71/90 |

FOREIGN PATENT DOCUMENTS

| | | |
|---|---|---|
| 2035757 | 12/1970 | France. |
| 1022750 | 3/1966 | United Kingdom. |
| 1137529 | 12/1968 | United Kingdom. |
| 1147626 | 4/1969 | United Kingdom. |

OTHER PUBLICATIONS

Polts, Comprehensive Heterocyclic Chemistry 6 p. 256 (1984).
McEvoy et al., J. Med. Chem. 15, 850 (1972).

Primary Examiner—Robert Gerstl
Attorney, Agent, or Firm—Joel G. Ackerman

[57] ABSTRACT

A method of killing or controlling unwanted plants by applying to the plant on to a locus thereof an effective amount of a compound of formula (I)

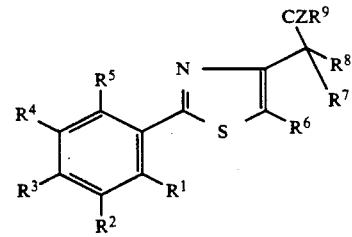

or a salt thereof: wherein $R^1$, $R^2$, $R^3$, $R^4$ and $R^5$ are independently selected from hydrogen, hydroxy, alkyl, alkoxy, alkylcarbonyl, halogen, cyans, nitro, haloalkyl and haloalkoxy; $R^6$ is hydrogen, hydroxy, amino, lower alkyl, halogen, cyano, haloalkyl, nitro, aryl, or a group $C(O)_m R^{10}$, wherein $R^{10}$ is hydrogen, alkyl, alkenyl, alkynyl or phenyl any of which may be optionally substituted and m is 1 or 2; $R^7$ is hydrogen, lower alkyl, haloalkyl, $C(O)_m R^{10}$ or halogen; or $R^6$ and $R^7$ together form an optionally substituted alkylene chain of 2 or 3 carbon atoms; $R^8$ is hydrogen, lower alkyl or halogen or the group $R^7$ or $R^8$ together form an oxo group; and the group $CZR^9$ is carboxy or an ester thereof, or $R^9$ is a group $SR^{10}$ or $NR^{11}R^{12}$ wherein $R^{11}$ is hydrogen or alkyl and $R^{12}$ is hydrogen, alkyl, $S(O)_n R^{10}$ wherein n is 0, 1 or 2; or $R^9$ is a group $NR^{11}NR^{13}R^{14}$ wherein $R^{11}$, $R^{13}$ and $R^{14}$ are independently selected from hydrogen or alkyl; or $R^9$ is a group $-N^{\oplus}R^{11}NR^{13}R^{14}$ $R^{20}$ $x^{\ominus}$ wherein $R^{11}$, $R^{13}$, $R^{14}$ and $R^{20}$ are each hydrogen or alkyl, and $x^-$ is an agricultrually acceptable anion, and Z is oxygen or sulphur.

Herbicidal compositions containing compounds of formula (I) are also claimed together with certain novel sub groups of compounds of formula (I) and processes for their preparation.

8 Claims, No Drawings

HERBICIDAL COMPOSITIONS

This is a divisional of application Ser. No. 07/432,104, filed Nov. 2, 1989 now U.S. Pat. No. 5,084,083.

The present invention relates to the use of certain thiazole derivatives as herbicides and herbicidal compositions containing these compounds. Some of these compounds are novel and these, together with processes for their preparation form a further aspect of the invention.

A large number of thiazole derivatives are known in particular as pharmaceuticals (see for example British Patent Number 1,099,389). British Patent Number 1,022,750 and U.S. Pat. No. 3,418,331 show that some are also known as herbicides.

According to the present invention there is provided a method for killing or controlling unwanted plants by applying to the plants or to locus thereof a herbicidally effective amount of a compound of formula (I)

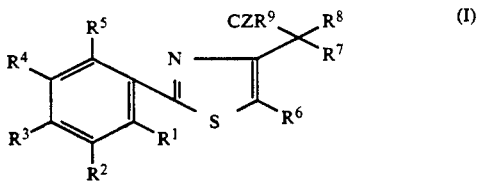

or a salt thereof; wherein $R^1$, $R^2$, $R^3$, $R^4$ and $R^5$ are independently selected from hydrogen, hydroxy, alkyl, alkoxy, alkylcarbonyl, halogen, cyano, nitro, haloalkyl and haloalkoxy; $R^6$ is hydrogen, hydroxy, amino, mono- or di-alkyl amino, lower alkyl, halogen, cyano, haloalkyl, nitro, aryl, or a group $C(O)_m R^{10}$ wherein $R^{10}$ is hydrogen, alkyl, alkenyl, alkynyl or phenyl any of which may be optionally substituted and $m$ is 1 or 2; $R^7$ is hydrogen, lower alkyl, haloalkyl, $C(O)_m R^{10}$ or halogen; or $R^6$ and $R^7$ together form an optionally substituted alkylene chain of 2 or 3 carbon atoms; $R^8$ is hydrogen, lower alkyl or halogen or the group $R^7$ and $R^8$ together form an oxo group; and the group $CZR^9$ is carboxy or an ester thereof, or $R^9$ is a group $SR^{10}$ or $NR^{11}R^{12}$ wherein $R^{11}$ is hydrogen or alkyl and $R^1$ is hydrogen, optionally substituted alkyl, aryl, $S(O)_n R^{10}$ where n is 0, 1 or 2, or $R^9$ is a group $-NR^{11}NR^{13}R^{14}$ wherein $R^{11}$, $R^{13}$ and $R^{14}$ are independently selected from hydrogen or alkyl; or $R^9$ is a group $-NR^{11}N\oplus R^{13}R^{14}R^{20}\ x\ \ominus$ wherein $R^{11}$, $R^{13}$, $R^{14}$ and $R^{20}$ are each hydrogen or alkyl and $X^-$ is an agriculturally acceptable anion; and Z is oxygen or sulphur.

Salts of the compounds of formula (I) are available when the compound includes a carboxy group. Suitable salts are agriculturally acceptable salts such as sodium, potassium, calcium, ammonium or sulphonium salts. Examples of ammonium salts are those of formula $NR^a R^b R^c R^d$ wherein $R^a$, $R^b$, $R^c$, and $R^d$, are independently selected from hydrogen or $C_{1-10}$ alkyl optionally substituted with for example hydroxy.

Examples of sulphonium salts include those of formula $R^a R^b R^c S$ where $R^a$, $R^b$ and $R^c$ are independently selected from optionally substituted $C_{1-10}$ alkyl.

As used herein the term "alkyl" includes straight or branched chains suitably containing from 1 to 10 carbon atoms, preferably from 1 to 6 carbon atoms. The expression "lower alkyl" refers to alkyl groups having from 1 to 3 carbon atoms. Similarly the terms alkenyl or "alkynyl" refer to unsaturated straight or branched chains having from 2 to 10, preferably from 2 to 6 carbon atoms. In addition the term "alkoxy" refers to group O-alkyl as defined above. The terms "haloalkyl" and "haloalkoxy" refer to the described alkyl groups and alkoxy groups respectively which are substituted by at least one halogen atom such as fluorine, chlorine, bromine or iodine. A particular haloalkyl group is trifluoromethyl and a particular haloalkoxy group is trifluoromethoxy.

As used herein the term "aryl" includes phenyl and naphthyl.

Suitable groups $R^1$, $R^2$, $R^3$, $R^4$ and $R^5$ are hydrogen, $C_{(1-6)}$ alkyl, $C_{(1-6)}$alkoxy, lower alkyl carbonyl, halo $C_{(1-6)}$ alkyl, halo $(C_{1-6})$ alkoxy or halo wherein the halo groups are selected from fluorine, chlorine, bromine and iodine.

Particular examples of the groups $R^1$, $R^2$, $R^3$, $R^4$ and $R^5$ are hydrogen, methyl, methoxy, trifluoromethyl trifluoromethoxy, fluoro, chloro, bromo, iodo or cyano.

In a particular embodiment $R^3$ is other than hydrogen. Preferably $R^3$ is halogen such as chlorine and $R^1$, $R^2$, $R^4$ and $R^5$ are hydrogen.

Suitably $R^6$ is lower alkyl such as methyl or ethyl, halogen such as fluorine, chlorine, bromine or iodine, amino, hydroxy, nitro, cyano, carboxy or lower alkyl esters thereof or trifluoromethyl. In particular $R^6$ is bromine or chlorine.

Suitably $R^7$ is selected from hydrogen, alkyl in particular lower alkyl, carboxy or lower alkyl esters thereof or haloalkyl such as trifluoromethyl or bromomethyl.

Suitably $R^8$ is selected from hydrogen or methyl.

Preferably both $R^7$ and $R^8$ are hydrogen.

When $R^6$ and $R^7$ form an optionally substituted alkylene chain, the substituents are suitably selected from those described above for $R^{15}$ below.

When the group $CZR^9$ is an ester of a carboxy group, it is suitably a group of formula $CO_2 R^{15}$ wherein $R^{15}$ is alkyl, alkenyl, alkynyl or phenyl any of which ay be optionally substituted.

Suitable optional substituents for $R^{15}$ include one or more groups selected from halo such as fluoro, chloro, bromo or iodo; hydroxy; $C_{1-6}$ alkoxy; $C_{(1-6)}$ alkoxy$C_{(1-6)}$alkoxy; aryl $C_{(1-6)}$alkoxy; nitro; cycloalkyl; heterocyclic optionally substituted by oxo; cyano; phenyl optionally substituted by nitro, halo such as chloro, alkoxy or carboxy or salts or $C_{1-6}$ alkyl esters thereof; or alkylsilyl groups such as trimethylsilyl.

As used herein the term "cycloalkyl" refers to cyclic alkyl groups containing from 3 to 10 ring carbon atoms. The term "heterocyclic" refers to rings of 3 to 10 atoms containing at least one atom selected from oxygen, nitrogen or sulphur.

When $R^{15}$ is an alkenyl or alkynyl group, it suitably contains from 2 to 10 carbon atoms, preferably from 2 to 6 carbon atoms.

Preferred groups $R^9$ are $OR^{16}$ where $R^{16}$ is hydrogen or unsubstituted $C_{1-6}$ alkyl.

Preferably Z is oxygen.

When $R^9$ is a group $SR^{10}$, $R^{10}$ is preferably an alkyl group such as lower alkyl in particular ethyl. When $R^9$ is a group $NR^{11} R^{12}$. $R^{11}$ and $R^{12}$, are suitably selected from hydrogen or lower alkyl such as methyl. $R^{12}$ may additionally be selected from phenyl, lower alkyl substituted by carboxy or lower alkyl esters thereof. $R^9$ may also be a group $-NR^{11}NR^{13}R^{14}$ where $R^{13}$ and $R^{14}$ are independently hydrogen or lower alkyl such as methyl, or $R^9$ may be a group $-NR^{11}N\oplus R^{13}R^{14}R^{20}\ X\ominus$.

Preferred groups $NR^{11}R^{12}$ are $NH_2, N(CH_3)_2$ or $NHNH_2$.

When $R^9$ is a group $-NR^{11}N^{\oplus}R^{13}R^{14}R^{20} \; X^{\ominus}$, $X^{\ominus}$ may be a halide anion, for example chloride, bromide or iodide.

Suitable substituents for $R^{10}$ include those described above for $R^{15}$.

Examples of compounds of formula (I) are set out in Tables I and II below. In all cases unless otherwise stated Z is oxygen.

TABLE I

| COMPOUND NO. | $R^1$ | $R^2$ | $R^3$ | $R^4$ | $R^5$ | $R^6$ | $R^7$ | $R^8$ | $R^9$ |
|---|---|---|---|---|---|---|---|---|---|
| 1 | H | H | Br | H | H | H | H | H | $NH_2$ |
| 2 | H | H | $CH_3$ | H | H | H | H | H | OH |
| 3 | H | H | Cl | H | H | H | H | H | OH |
| 4 | H | H | Cl | H | H | Cl | H | H | OH |
| 5 | H | H | Br | H | H | H | H | H | $OCH_2CH_3$ |
| 6 | H | Cl | Cl | H | H | H | H | H | OH |
| 7 | H | H | Cl | H | H | H | H | H | $OCH_3$ |
| 8 | H | H | Cl | H | H | H | H | H | $OCH_2CH_3$ |
| 9 | H | H | Cl | H | H | Br | H | H | OH |
| 10 | H | $CH_3$ | Cl | H | H | H | H | H | OH |
| 11 | H | H | Cl | H | H | H | $CH_3$ | $CH_3$ | OH |
| 12 | H | $OCH_3$ | Cl | H | H | H | H | H | OH |
| 13 | H | H | Cl | H | H | H | H | H | $NH-NH_2$ |
| 14 | H | H | Cl | H | H | Cl | H | H | $OCH_3$ |
| 15 | H | H | Cl | H | H | Cl | H | H | $O(CH_2)_2CH_3$ |
| 16 | H | H | Cl | H | H | Cl | H | H | $NH_2$ |
| 17 | H | H | Cl | H | H | Br | H | H | $OCH_3$ |
| 18 | H | H | Cl | H | H | Br | H | H | $O(CH_2)_2CH_3$ |
| 19 | H | H | Cl | H | H | Br | H | H | $OCH_2CH_3$ |
| 20 | H | H | Cl | H | H | Cl | H | H | $OCH_2CH_3$ |
| 21 | H | H | Cl | H | H | Cl | H | H | $NHNH_2$ |
| 22 | H | H | H | H | H | H | H | H | $N(CH_3)_2$ |
| 23 | H | H | Cl | H | H | H | H | H | $N(CH_3)_2$ |
| 24 | H | H | H | H | H | H | $CH_3$ | H | $N(CH_3)_2$ |
| 25 | H | H | Cl | H | H | H | H | H | $NHCH_2CH_3$ |
| 26 | H | H | H | H | H | H | H | H | $N(CH_2CH_3)_2$ |
| 27 | H | H | H | H | H | H | H | H | $NHCH_2CH_3$ |
| 28 | H | H | H | H | H | Cl | H | H | $N(CH_3)_2$ |
| 29 | Cl | H | H | H | H | H | H | H | $CH_2CH_3$ |
| 30 | Cl | H | H | H | H | H | H | H | $N(CH_3)_2$ |
| 31 | H | H | H | H | H | H | $CH_3$ | $CH_3$ | $N(CH_3)_2$ |
| 32 | Cl | H | H | H | Cl | H | H | H | $N(CH_3)_2$ |
| 33 | Cl | H | H | H | Cl | H | $CH_3$ | H | $N(CH_3)_2$ |
| 34 | Cl | H | H | H | H | H | $CH_3$ | $CH_3$ | $N(CH_3)_2$ |
| 35 | $CH_3$ | H | H | H | H | H | H | H | $N(CH_3)_2$ |
| 36 | $CH_3$ | H | H | H | H | H | $CH_3$ | H | $N(CH_3)_2$ |
| 37 | Cl | H | H | H | H | H | $CH_3$ | H | $N(CH_3)_2$ |
| 38 | $CF_3$ | H | H | H | H | H | H | H | OH |
| 39 | Cl | H | H | H | H | H | H | H | $N(CH_3)_2$ |
| 40 | F | H | H | H | F | H | H | H | $OCH_2CH_3$ |
| 41 | F | H | H | H | F | H | H | H | OH |
| 42 | F | H | H | H | F | H | H | H | $N(CH_3)_2$ |
| 43 | Cl | H | H | H | Cl | H | H | H | $OCH_2CH_3$ |
| 44 | Cl | H | H | H | F | H | H | H | $OCH_2CH_3$ |
| 45 | Br | H | H | H | H | H | H | H | $OCH_2CH_3$ |
| 46 | Br | H | H | H | H | H | H | H | OH |
| 47 | Br | H | H | H | H | H | H | H | $N(CH_3)_2$ |
| 48 | Cl | H | H | H | F | H | H | H | OH |
| 49 | Cl | H | H | H | F | H | H | H | $N(CH_3)_2$ |
| 50 | Cl | H | H | H | Cl | H | H | H | $NHNH_2$ |
| 51 | Cl | H | H | $CF_3$ | H | H | H | H | $OCH_3CH_3$ |
| 52 | Cl | H | H | $CF_3$ | H | H | H | H | OH |
| 53 | Cl | H | H | $CF_3$ | H | H | H | H | $N(CH_3)_2$ |
| 54 | $CH_2CH_3$ | H | H | H | H | H | H | H | $OCH_2CH_3$ |
| 55 | H | Br | Br | H | H | H | H | H | OH |
| 56 | H | H | Cl | H | H | $CH_2CH_3$ | H | H | $OCH_2CH_3$ |
| 57 | H | H | Cl | H | H | $CH_3$ | H | H | $OCH_2CH_3$ |
| 58 | H | H | Cl | H | H | H | $CH_3$ | H | $OCH_2CH_3$ |
| 59 | H | H | Cl | H | H | H | $CH(CH_3)_2$ | H | $OCH_2CH_3$ |
| 60 | H | H | Cl | H | H | Br | $CH(CH_3)_2$ | H | $OCH_2CH_3$ |
| 61 | H | H | Cl | H | H | Cl | $CH_3$ | H | $OCH_2CH_3$ |
| 62 | H | H | Cl | H | H | Cl | H | H | $N(CH_3)_2$ |
| 63 | H | H | Cl | H | H | Cl | H | H | $NHN(CH_3)_2$ |
| 64 | H | H | Cl | H | H | Br | H | H | $OCH(CH_3)_2$ |
| 65 | H | H | Cl | H | H | Br | H | H | $O(CH_2)_3CH_3$ |
| 66 | H | H | $CF_3$ | H | H | H | H | H | $OCH_2CH_3$ |
| 67 | H | H | I | H | H | H | H | H | $OCH_2CH_3$ |
| 68 | H | H | Cl | H | H | Cl | H | H | $NHSO_2CH_3$ |
| 69 | H | H | Cl | H | H | Br | H | H | $NHC_6H_5$ |
| 70 | H | H | I | H | H | Br | H | H | $OCH_2CH_3$ |
| 71 | H | H | Cl | H | H | Br | H | H | $OCH_2CH_2OCH_3$ |
| 72 | H | H | Cl | H | H | Br | H | H | $OCH_2CH_2OH$ |
| 73 | H | H | Cl | H | H | Cl | H | H | $OCH_2CH_2CH(CH_3)_2$ |
| 74 | H | H | Cl | H | H | Cl | H | H | $OCH_2CH=CH_2$ |

TABLE I-continued

| COMPOUND NO. | $R^1$ | $R^2$ | $R^3$ | $R^4$ | $R^5$ | $R^6$ | $R^7$ | $R^8$ | $R^9$ |
|---|---|---|---|---|---|---|---|---|---|
| 75 | H | H | Cl | H | H | Cl | H | H | OCH(CH$_2$CH$_3$)CH$_2$CH$_3$ |
| 76 | H | H | Cl | H | H | Cl | H | H | OCH$_2$C≡CH |
| 77 | H | H | Cl | H | H | Cl | H | H | O(CH$_2$)$_4$CH$_3$ |
| 78 | H | H | Cl | H | H | Cl | H | H | OCH$_2$CH(CH$_3$)—(CH$_2$)$_3$CH(CH$_3$)$_2$ |
| 79 | H | H | Cl | H | H | Cl | H | H | OCH$_2$CH$_2$OCH$_2$(C$_6$H$_5$) |
| 80 | H | H | Cl | H | H | Cl | H | H | OCH$_2$C(CH$_3$)$_3$ |
| 81 | H | H | Cl | H | H | Cl | H | H | OCH$_2$CH(CH$_3$)$_2$ |
| 82 | H | H | Cl | H | H | Cl | H | H | OCH$_2$CH(CH$_2$CH$_3$)CH$_3$ |
| 83 | H | H | Cl | H | H | Cl | H | H | OCH(CH$_3$)CH$_2$CH$_2$CH$_3$ |
| 84 | H | H | Cl | H | H | Cl | H | H | OCH(CH$_3$)CH(CH$_3$)$_2$ |
| 85 | H | H | Cl | H | H | Cl | H | H | OCH(CH$_3$)CH$_2$CH$_3$ |
| 86 | H | H | Cl | H | H | Cl | H | H | OCH$_2$(C$_6$H$_{11}$) |
| 87 | H | H | Cl | H | H | Cl | H | H | OCH(CH$_3$)CH$_2$OCH$_3$ |
| 88 | H | H | Cl | H | H | Cl | H | H | O(CH$_2$)$_5$CH$_3$ |
| 89 | H | H | Cl | H | H | Cl | H | H | OCH$_2$CH$_2$CH(OCH$_3$)CH$_3$ |
| 90 | H | H | Cl | H | H | Cl | H | H | OCH$_2$C$_6$H$_5$ |
| 91 | H | H | Cl | H | H | Cl | H | H | O—C$_6$H$_4$—OCH$_3$ |
| 92 | H | H | Cl | H | H | Cl | H | H | O(CH$_2$)$_7$CH$_3$ |
| 93 | H | H | Cl | H | H | Cl | H | H | O—C$_6$H$_4$—NO$_2$ |
| 94 | H | H | Cl | H | H | Cl | H | H | O(CH$_2$)$_9$CH$_3$ |
| 95 | H | H | Cl | H | H | Cl | H | H | OC$_6$H$_5$ |
| 96 | H | H | Cl | H | H | Br | H | H | OCH$_2$C(CH$_3$)$_3$ |
| 97 | H | H | Cl | H | H | Br | H | H | OCH(CH$_3$)CH$_2$OCH$_3$ |
| 98 | H | H | Cl | H | H | Br | H | H | OC$_6$H$_5$ |
| 99 | H | H | Cl | H | H | Br | H | H | OCH$_2$C$_6$H$_5$ |
| 100 | H | H | Cl | H | H | Br | H | H | OCH$_2$C$_6$H$_{11}$ |
| 101 | H | H | Cl | H | H | Br | H | H | O—C$_6$H$_4$—OCH$_3$ |
| 102 | H | H | Cl | H | H | Br | H | H | O(CH$_2$)$_7$CH$_3$ |
| 103 | H | H | Cl | H | H | Cl | H | H | OC(CH$_3$)$_3$ |
| 104 | H | H | Cl | H | H | Cl | H | H | OCH$_2$C(CH$_3$)$_2$CH$_2$Cl |
| 105 | H | H | Cl | H | H | Cl | H | H | OCH$_2$Si(CH$_3$)$_3$ |
| 106 | H | H | Cl | H | H | Cl | H | H | OC(CH$_3$)$_2$CH$_2$Cl |
| 107 | H | H | Cl | H | H | Cl | H | H | OCH$_2$CH$_2$OCH$_2$CH$_2$OCH$_3$ |
| 108 | H | H | Cl | H | H | Cl | H | H | OCH$_2$CO$_2$CH$_2$CH$_3$ |
| 109 | H | H | Cl | H | H | Cl | H | H | OCH$_2$CHOCH$_2$CH$_2$CH$_2$ |
| 110 | H | H | Cl | H | H | Cl | H | H | OCH(C$_6$H$_5$)CO$_2$CH$_2$CH$_3$ |
| 111 | H | H | Cl | H | H | Br | H | H | OCHCH$_2$CH$_2$OC=O |
| 112 | H | H | Cl | H | H | Br | H | H | OCH(CH$_3$)CO$_2$CH$_3$ |
| 113 | H | H | Cl | H | H | Br | H | H | OCH$_2$(C$_6$H$_5$)CO$_2$CH$_2$CH$_3$ |
| 114 | H | H | Cl | H | H | Br | H | H | OCH$_2$CO$_2$CH$_2$CH$_3$ |
| 115 | H | H | Cl | H | H | Br | H | H | O(CH$_2$)$_2$O(CH$_2$)$_2$OCH$_3$ |
| 116 | H | H | Cl | H | H | Br | H | H | OCH(C$_6$H$_5$)CO$_2$CH$_3$ |
| 117 | H | H | Cl | H | H | Cl | H | H | OCH(C$_6$H$_5$)CO$_2$CH$_3$ |
| 118 | H | H | Cl | H | H | Cl | H | H | OC(CH$_3$)$_2$CF$_2$CF$_2$H |
| 119 | H | H | Cl | H | H | Cl | H | H | OCH(CH$_3$)CO$_2$CH$_3$ |
| 120 | H | H | Cl | H | H | Cl | H | H | NHCH$_2$CO$_2$CH$_2$CH$_3$ |
| 121 | H | H | Cl | H | H | Cl | H | H | OCHCH$_2$CH$_2$OC=O |
| 122 | H | H | Cl | H | H | Cl | Br | H | OCH$_2$CH$_3$ |
| 123 | H | H | Cl | H | H | Cl | CO$_2$C$_6$H$_5$ | H | OCH$_2$CH$_3$ |
| 124 | H | H | Cl | H | H | Cl | Cl | H | OCH$_2$CH$_3$ |
| 125 | H | H | Cl | H | H | Cl | =O | | OCH$_2$CH$_3$ |

TABLE I-continued

| COMPOUND NO. | R¹ | R² | R³ | R⁴ | R⁵ | R⁶ | R⁷ | R⁸ | R⁹ |
|---|---|---|---|---|---|---|---|---|---|
| 126 | H | H | Cl | H | H | NO₂ | H | H | OCH₃ |
| 127 | H | H | F | H | H | Br | H | H | OCH₃ |
| 128 | H | H | F | H | H | Br | H | H | OCH₂CH₃ |
| 129 | H | H | Cl | H | H | Br | H | H | O(CH₂)₄CH₃ |
| 130 | H | H | Cl | H | H | Br | H | H | O(CH₂)₅CH₃ |
| 131 | H | H | Cl | H | H | Br | H | H | O(CH₂)₇CH₃ |
| 132 | H | H | Cl | H | H | Cl | F | H | OCH₂CH₃ |
| 133* | H | H | Cl | H | H | Br | H | H | OCH₃ |
| 134 | F | H | H | H | F | Br | Br | H | OCH₂CH₃ |
| 135 | H | CH₃ | H | H | H | H | H | H | OCH₃ |
| 136 | H | H | F | H | H | H | H | H | OCH₃ |
| 137 | H | H | F | H | H | NO₂ | H | H | OCH₃ |
| 138 | H | H | Cl | H | H | Br | H | H | O(CH₂)₂CH₃ |
| 139 | H | H | F | H | H | H | H | H | OCH₃ |
| 140 | H | Cl | H | H | H | Br | H | H | OH |
| 141 | H | H | H | H | H | Br | H | H | OCH₂CH₃ |
| 142 | H | H | H | H | H | Br | H | H | OCH₃ |
| 143 | H | Cl | H | H | H | Br | H | H | OCH₂CH₃ |
| 144 | H | Cl | H | H | H | Br | H | H | OCH₃ |
| 145 | H | H | Cl | H | H | Br | Br | H | OCH₃ |
| 146 | H | H | Cl | H | H | Br | Br | H | OCH₂CH₃ |
| 147 | H | H | Br | H | H | Br | H | H | OCH₃ |
| 148 | H | H | Br | H | H | Br | H | H | OCH₂CH₃ |
| 149 | H | H | Br | H | H | Br | H | H | O(CH₂)₂CH₃ |
| 150 | H | H | Br | H | H | Br | H | H | OH |
| 151 | H | H | CF₃ | H | H | Br | H | H | OH |
| 152 | H | H | CF₃ | H | H | Br | H | H | OCH₃ |
| 153 | H | H | CF₃ | H | H | Br | H | H | OCH₂CH₃ |
| 154 | H | H | Cl | H | H | NH₂ | H | H | OCH₃ |
| 155 | F | H | F | H | H | Br | H | H | OH |
| 156 | H | F | F | H | H | Br | H | H | OH |
| 157 | F | H | F | H | H | Br | H | H | OCH₃ |
| 158 | F | H | F | H | H | Br | H | H | OCH₂CH₃ |
| 159 | H | F | F | H | H | Br | H | H | OCH₃ |
| 160 | H | F | F | H | H | Br | H | H | OCH₂CH₃ |
| 161 | H | H | NO₂ | H | H | H | H | H | OH |
| 162 | H | H | H | H | H | Br | H | H | OH |
| 163 | H | H | F | H | H | Br | H | H | OH |
| 164 | F | H | H | H | F | Br | H | H | N(CH₃)₂ |
| 165 | H | H | Cl | H | H | Br | H | H | NHN(CH₃)₂ |
| 166 | H | H | Cl | H | H | Br | H | H | $\overset{\oplus}{N}HN(CH_3)_3 I^{\ominus}$ |
| 167 | H | H | CH₃ | H | H | Br | H | H | OCH₃ |
| 168 | H | H | Cl | H | H | Br | H | H | SCH₂CH₃ |
| 169 | H | H | OCH₃ | H | H | Br | H | H | OCH₃ |
| 170 | H | H | OCH₃ | H | H | Br | H | H | OH |
| 171 | H | H | OCF₃ | H | H | Br | H | H | OCH₃ |
| 172 | H | H | COCH₃ | H | H | Br | H | H | OH |
| 173 | H | H | Cl | H | H | H | F | H | OCH₃ |
| 174 | H | H | OH | H | H | Br | H | H | OCH₃ |
| 175 | H | H | Cl | H | H | CO₂CH₃ | H | H | OCH₃ |
| 176 | H | H | Cl | H | H | CO₂H | H | H | OH |
| 177 | H | H | Cl | H | H | OH | H | H | OH |
| 178 | H | H | Cl | H | H | CH₃ | CH₃ | H | OCH₃ |
| 179 | H | H | Cl | H | H | CH₂Br | CH₃ | H | OCH₃ |

*Z = sulphur

TABLE II

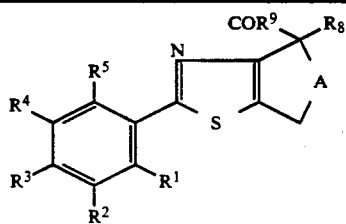

| COMPOUND NO. | R¹ | R² | R³ | R⁴ | R⁵ | R⁸ | R⁹ | A |
|---|---|---|---|---|---|---|---|---|
| 180 | H | H | Cl | H | H | H | OCH₂CH₃ | —CH₂— |
| 181 | H | H | Cl | H | H | H | OH | —CH₂— |
| 182 | H | H | Cl | H | H | H | OCH(CH₃)₂ | —CH₂— |
| 183 | H | H | H | H | H | H | OCH₂CH₃ | —CH₂— |
| 184 | H | H | C(CH₃)₃ | H | H | H | OCH₂CH₃ | —CH₂— |

TABLE II-continued

COMPOUND NO. | R¹ | R² | R³ | R⁴ | R⁵ | R⁸ | R⁹ | A
---|---|---|---|---|---|---|---|---
185 | H | H | CF₃ | H | H | H | OCH₂CH₃ | —CH₂—
186 | H | H | Cl | H | H | H | OCH₂CH₃ | —CH₂—CH₂—
187 | H | H | H | H | H | H | OCH₂CH₃ | —CH₂—CH₂—
188 | H | Cl | F | H | H | H | OCH₂CH₃ | —CH₂—
189 | H | Cl | F | H | H | H | OCH₂CH₃ | —CH₂—CH₂—
190 | H | H | Br | H | H | H | OCH₂CH₃ | —CH₂—CH₂—
191 | Cl | H | H | H | H | H | OCH₂CH₃ | —CH₂—CH₂—
192 | H | H | Br | H | H | H | OCH₂CH₃ | —CH₂—
193 | Cl | H | H | H | Cl | H | OCH₂CH₃ | —CH₂—CH₂—
194 | H | H | CH₃ | H | H | H | OCH₂ | —CH₂—CH₂—
195 | Cl | H | Cl | H | H | H | OCH₂CH₃ | —CH₂—CH₂—
196 | Cl | H | H | H | F | H | OCH₂CH₃ | —CH₂—
197 | H | H | F | H | H | H | OCH₂CH₃ | —CH₂—

Many of the compounds of formula (I) are known compounds and can be prepared by known methods for example as set out in GB Patent Number 1,099,389. An example of preparation is set out in Scheme A below. The reaction conditions employed in each step of the process are conventional.

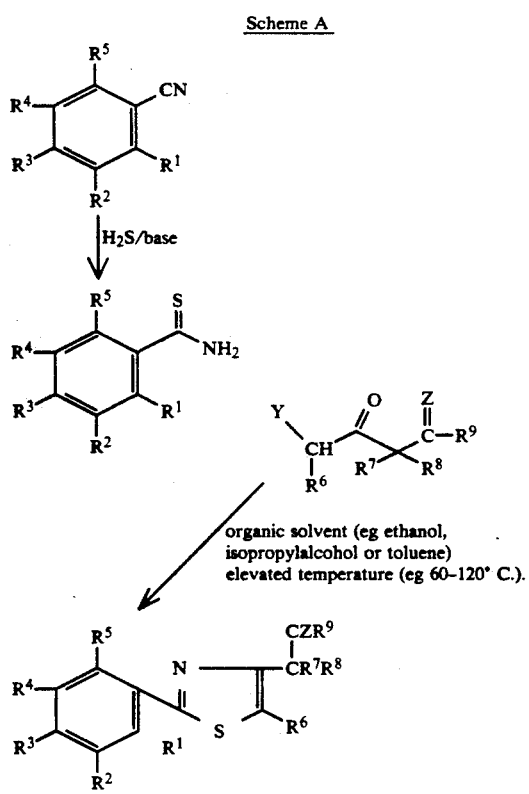

In scheme A, $R^1$, $R^2$, $R^3$, $R^4$, $R^5$, $R^6$, $R^7$, $R^8$, $R^9$ and Z are as defined in relation to formula (I), Y is a leaving group such as chloro, and $R^6$ is H, lower alkyl, or —CO₂R¹⁰.

Certain of the compounds of formula (I) are novel and these form a further aspect of the invention.

In particular according to the invention there is provided a compound of formula (II)

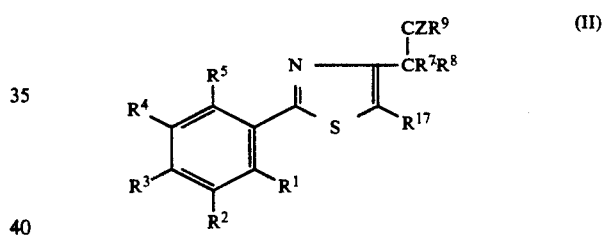

wherein $R^1$, $R^2$, $R^3$, $R^4$, $R^5$, $R^7$, $R^8$ $R^9$ and Z are as defined in relation to formula (I) and $R^{17}$ is halogen, nitro, hydroxy, amino, mono-or di-alkylamino or cyano.

In a preferred embodiment $R^{17}$ is halogen such as fluoro, chloro, bromo, or iodine preferably bromo.

Compounds of formula (II) where $R^{17}$ is halogen can be prepared by reacting a compound of formula (III)

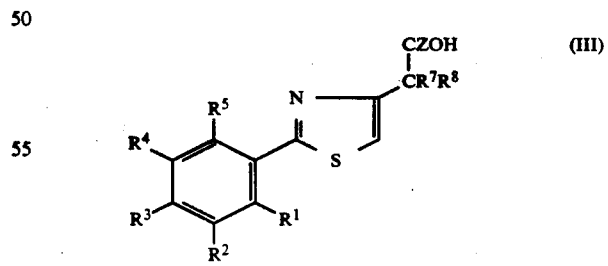

wherein $R^1$, $R^2$, $R^3$, $R^4$, $R^5$, $R^7$ $R^8$ and Z are as defined in relation to formula (I); with chlorine or bromine and thereafter if necessary converting the group CZOH to a different group $CZR^9$ as defined in relation to formula (I).

The reaction is suitably carried out in a solvent such as glacial acetic acid and/or chloroform at temperatures of from 20°-80° C.

Compounds of formula II where $R^{17}$ is nitrile can be prepared by subjecting the products of Scheme A wherein $R^6$ is $-CO_2R^{10}$ to conventional procedures for transforming an alkoxy-carbonyl group to a $-CN$ group.

Compounds of formula (II) where $R^{17}$ is nitro can be prepared by reacting an ester derivative of a compound of formula (III) with a mild nitrating agent such as nitronium tetrafluoroborate. The reaction is suitably effected in an organic solvent such as $CH_3CN$. Low temperatures of from 0° C.–15° C. are suitably employed.

These nitro compounds can be converted to compounds of formula (II) where $R^{17}$ is amino by hydrogenation using conventional conditions. For instance, the compound can be reacted with hydrogen in the presence of a catalyst such as palladium on charcoal. The reaction is suitably effected in an organic solvent such as methanol or dichloromethane. Alkylation of the amino compound for example by reaction with an alkyl halide in the presence of base gives a compound of formula (II) where $R^{17}$ is the mono- or di-alkyl amino group.

Compounds of formula (III) are known compounds and fall within the definition of formula (I), or can be prepared from known compounds by conventional methods.

Conversion of the group CZOH to a $CZR^9$ group can be carried out by conventional methods. One simple method for preparing a compound of formula (I) where $R^9$ is $OR^{10}$ and $R^{10}$ is lower alkyl is by refluxing the compound in an appropriate alcohol of formula $R^{19}OH$ wherein $R^{19}$ is alkyl such as methanol or ethanol, in the presence of a catalytic amount of acid such as sulphuric acid.

Alternatively the compound can be reacted with an appropriate alcohol, dicyclohexylcarbodiimide (DCC) as a coupling agent, in the presence of a base such as DMAP. The reaction may be carried out in an organic solvent such as dichloromethane or chloroform. Low temperatures, for example from −5° to 20° C. are suitably employed.

Other compounds of formula (I) which are novel and which form an additional aspect of the invention are compounds of formula (V)

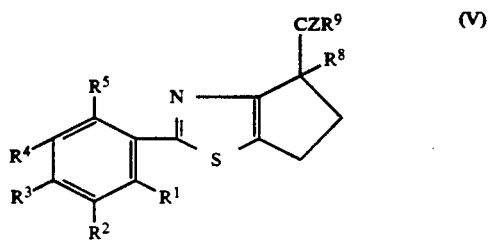

wherein $R^1$, $R^2$, $R^3$, $R^4$, $R^5$, $R^8$, $R^9$ and Z are as defined in relation to formula (I)

The compounds are prepared by reacting a compound of formula (VI)

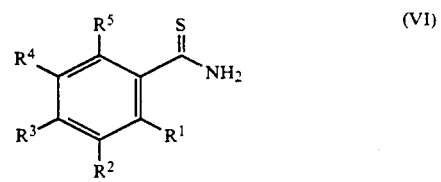

wherein $R^1$, $R^2$, $R^3$, $R^4$ and $R^5$ are as defined in relation to formula (I); with a compound of formula (VII)

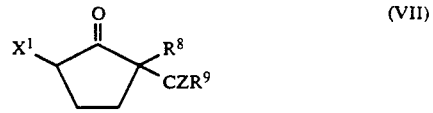

wherein $R^8$, $R^9$ and Z are as defined in relation to formula (I), and $X^1$ is a leaving group such as chlorine or bromine.

The reaction is suitably carried out in an organic solvent such as ethanol or toluene at elevated temperatures from 60° to 120° C.

Compounds of formula (VI) and (VII) are either known compounds or they can be prepared from known compounds by conventional methods.

The compounds of formula (I) are active as herbicides and therefore, in a further aspect the invention provides a process for severely damaging or killing unwanted plants which process comprises applying to the plants, or to the growth medium of the plants, an effective amount of a compound of formulae (I) as hereinbefore defined.

The compounds of formula (I) are active against a broad range of weed species including monocotyledenous and dicotyledonous species. The compounds may show a useful selectivity into monocotyledonous crops, in particular rice.

The compounds of formula (I) may be applied directly to the plant (post-emergence application) or to the soil before the emergence of the plant (pre-emergence application).

The compounds of formulae (I) may be used on their own to inhibit the growth of, severely damage, or kill plants but are preferably used in the form of a composition of the invention.

Compositions containing compounds of formula (I) include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01% to 2% of active ingredient, while concentrated compositions may contain from 20 to 90% of active ingredient, although from 20 to 70% is usually preferred.

The solid compositions may be in the form of granules, or dusting powders wherein the active ingredient is mixed with a finely divided solid diluent, e.g., kaolin, bentonite, kieselguhr, dolomite, calcium carbonate, talc, powdered magnesia Fuller's earth and gypsum. They may also be in the form of dispersible powders of grains, comprising a wetting agent to facilitate the dispersion of the powder or grain in liquid. Solid compositions in the form of a powder may be applied as foliar dusts.

Liquid compositions may comprise a solution or dispersion of an active ingredient in water optionally containing a surface-active agent, or may comprise a solution of dispersion of an active ingredient in a water-immiscible organic solvent which is dispersed as droplets in water.

Surface-active agents may be of the cationic, anionic, or non-ionic type. The cationic agents are, for example, quaternary ammonium compounds (e.g. cetyltrimethylammonium bromide). Suitable anionic agents are soaps; salts or aliphatic mono esters of sulphuric acid, for example sodium lauryl sulphate; and salts of sulphonates aromatic compounds, for example sodium dodecylbenzenesulphonate, sodium, calcium and ammonium lignosulphonate, butylnaphthalene sulphonate, and a mixture of the sodium of diisopropyl and triisopropl-naphthalenesulphonic acid. Suitable non-ionic agents are the condensation products of ethylene oxide with fatty alcohols such as oleyl alcohol and cetyl alcohol, or with alkylphenols such as octyl- or nonyl-phenol or octyl-cresol. Other non-ionic agents are the partial esters derived from long chain fatty acids and hexitol anhydrides, for example sorbitan monolaurate; the condensation products of the partial ester with ethylene oxide; and the lecithins.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene di-chloride, isopropyl. alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proporation of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprising the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties too, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.01 to 10 kilogrames per hectare is suitable.

The compositions of the invention may comprise, in addition to one or more compounds of formula (I) or (II) one or more compounds not of the invention but which possess biological activity. Accordingly in yet a still further embodiment the invention provides a herbicidal composition comprising a mixture of at least one herbicidal compound of formula (I) as hereinbefore defined with at least one other herbicide.

The other herbicide may be any herbicide not having the formula (I). It will generally be a herbicide having a complementary action in the particular application.

For example it may be desirable in certain circumstances to use the compound of formula (I) in admixture with a contact herbicide.

Examples of useful complementary herbicides include:

A. benzo-2,1,3-thiodiazin-4-one-2,2-dioxides such as 3-isopropylbenzo-2,1,3-thiadiazin-4-one-2, 2-dioxide (bentazon);

B. hormone herbicides, particularly the phenoxy alkanoic acids such as 4-chloro-2-methylphenoxy acetic acid (MCPA), S-ethyl 4-chloro-O-tolyloxy thio-acetate (MCPA-thioethyl), 2-(2,4-dichlorophenoxy) propionic acid (dichlorprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy) propionic acid (mecoprop), 3,5,6-trichloro-2-pyridyloxyacetic acid (trichlopyr), 4-amino-3,5-dichloro-6-fluoro-2-pyridyloxyacetic acid (fluroxypyr), 3,6-dichloropyridine-2-carboxylic acid (clopyralid), and their derivatives (e.g. salts, esters and amides);

C. 1,3 dimethylpyrazole derivatives such as 2-[4-(2,4-dichlorobenzoyl) 1,3-dimethylpyrazol-5-yloxy] acetophenone (pyrazoxyfen), 4-(2,4-dichlorobenzoyl)1,3-dimethylpyrazol-5-yltoluene suphonate (pyrazolate) and 2-[4-(2,4-dichloro-m-toluolyl)-1,3-dimethylpyrazol-5-yloxy[-4'-methylacetophenone (benzofenap);

D. Dinitrophenols and their derivatives (e.g. acetates such as 2-methyl-4,6-dinitrophenol (DNOC), 2-t-butyl-4,6-dinitrophenol (dinoterb), 2-secbutyl-4,6-dinitrophenol (dinoseb) and its ester, dinoseb acetate;

E. Dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin),
N-ethyl-N-(2-methylallyl)-2,6-dinitro-4-trifluoromethylaniline (ethalflurolin), N-(1-ethylpropyl)-2,6-dinitro-3,4-xylidine (pendimethalin); and 3,5-dinitro-$N^4$, $N^4$-dipropylsulphanilamide (oryzalin);

F. Arylurea herbicides such as N'-(3,4-dichlorophenyl)N,N-dimethylurea (diuron), N,N-dimethyl-N'-[3-(trifluoromethyl) phenyl]urea (flumeturon), 3-(3-chloro-4-methoxyphenyl)-1, 1-dimethylurea(metoxuron), 1-butyl-3-(3,4-dichlorophenyl)-1-methylurea(neburon), 3-(4-isopropylphenyl)-1,1-dimethylurea (isoproturon), 3-(3-chloro-p-tolyl)-1,1-dimethylurea (chlorotoluron), 3-[4-(4- chlorophenoxy) phenyl]-1, 1-dimethylurea (chloroxuron), 3-(3,4-dichlorophenyl)-1-methylurea (linuron), 3-(4-chlorophenyl)-1-methoxy-1-methylurea (monolinuron), 3-(4-bromo-4-chlorophenyl)-1-methoxy-1-methylurea (chlorbromuron), 1-(1-methyl-1-phenylethyl)-3-p-tolylurea(daimuron), and 1-benzothiazol-2-yl-1,3-dimethylurea (methabenzthiazuron);

G. phenylcarbamoyloxyphenylcarbamates such as 3-[methoxycarbonylamino]phenyl (3-methylphenyl)-carbamate (phenmedipham) and 3-[ethoxycarbonylamino]-phenyl phenylcarbamate (desmedipham);

H. 2-phenylpyridazin-3-ones such as 5-amino-4-chloro-2-phenylpyridazin-3-one (pyrazon), and 4-chloro-5-methylamino-2-($\alpha,\alpha,\alpha$-trifluoro-m-tolyl) pyridazin-3(2H)-one (norfluarazon);

I. uracil herbicides such as 3-cyclohexyl-5,6-trimethyleneuracil (lenacil), 5-bromo-3-sec-butyl-6-methyl-uracil (bromacil) and 3-t-butyl-5-chloro-6-methyl-uracil (terbacil);

J. triazine herbicides such as 2-chloro-4-ethylamino-6-(i-propylamino)-1,3,5-triazine (atrazine), 2-chloro-4,6-di(ethylamino)-1,3,5-triazine (simazine), 2-azido-4-(i-propylamino)-6-methylthio-1,3,5-triazine (aziprotryne), 2-(4-chloro-6-ethylamino-1,3,5-triazin-2-ylamino)-2-methylpropionitrile (cyanazine), $N^2$, $N^4$-di-isopropyl-6-methylthio-1,3,5-triazine-2,4-diamine (prometryne), $N^2$-(1,2-dimethylpropyl) -$N^4$-ethyl-6-methylthio-1,3,5-triazine-2,4-diamine (dimethametryne), $N^2,N^4$-diethyl-6-methylthio-1,3,5-triazine-2,4-diamine (simetryne), and $N^2$-tert-butyl-$N^4$-ethyl-6-methylthio-1,3,5-triazine-2,4-diamine (terbutryne); K. phosphorothioate herbicides such as S-2-methylpiperidinocarbonyl-methyl O,O-dipropyl phosphorodithioate (piperophos), S-2-benzenesulphonamidoethyl O,O-di isopropyl phosphonodithioate (bensulide), and O-ethyl O-6-nitro-m-tolyl sec-butylphosphoamidothioate (butamifos);

L. thiolcarbamate herbicides such as a S-ethyl N-cyclohexyl-N-ethyl(thiocarbamate) (cycloate), S-propyl dipropyl-thiocarbamate (vernolate), S-ethyl-azepine-1-carbothioate (molinate), S-4-chlorobenzyl diethylthiocarbamate (thiobencarb), S-ethyl di-isobutyl-thiocarbamate (butylate)*, S-ethyl diisopropylthiocarbamate (EPTC)*, S-2,3,3-trichloroallyl di-isopropyl (thiocarbamate) (tri-allate), S-2, 3-dichloroallyl di-isopropyl (thio-carbamate) (diallate), S-benzyl 1,2-dimethylpropyl (ethyl) thiocarbamate (esprocarb), S-benzyl di(sec-butyl)thiocarbamate (tricarbazil), 6-chloro-3-phenylpyridazin 4-yl S-octyl thiocarbamate (pyridate), and S-1-methyl-1-phenylethylpiperidine -1-carbothioate (dimepiperate);

* These compounds are preferably employed in combination with a safener such as 2,2-dichloro -N,N-di-2-propenylacetamide (dichlormid)

M. 1,2,4-triazin-5-one herbicides such as 4-amino-4,5-dihydro-3-methyl-6-phenyl-1,2,4-triazine -5-one(-metamitron) and 4-amino-6-t-butyl-4,5-dihydro-3-methylthio-1,3,4-triazin-5-one (metribuzin);

N. benzoic acid herbicides such as 2,3,6-trichlorobenzoic acid (2,3,6-TBA), 3,6-dichloro-2-methoxy-benzoic acid (dicamba) and 3-amino-2, 5-dichlorobenzoic acid (chloramben);

O. anilide herbicides such as 2-chloro-2',6'-diethyl-N-(2-propoxyethyl)acetanilide (pretilachlor), N-butoxymethyl-chloro-2', 6'-diethylacetanilide (butachlor), the corresponding N-methoxy compound (alachlor), the corresponding N-i-propyl compound (propachlor), 3',4'-dichloropropionilide (propanil), 2-chloro-N-[pyrazol-1-ylmethyl]acet-2'-6'xylidide (metazachlor),2-chloro-6'-ethyl-N-(2-methoxy-1-methylethyl)acet-0-toluidide (metolachlor), 2-chloro-N-ethoxymethyl-6'-ethylacet-0-toluidide (acetochlor), and 2-chloro-N-(2-methoxyethyl)acet-2',6'-xylidide (dimethachlor);

P. dihalobenzonitrile herbicides such as 2,6-dichloro-benzonitrile (dichlobenil), 3,5-dibromo-4-hydroxy-benzonitrile (bromoxynil) and 3,5-diiodo-4-hydroxy-benzonitrile (ioxynil);

Q. haloalkanoic herbicides such as 2,2-dichloropropionic acid (dalapon), trichloroacetic acid (TCA) and salts thereof;

R. diphenylether herbicides such as ethyl 2-[5-(2-chloro-trifluoro-p-tolyloxy)-2-nitrobenzoylooxy]propionate (lactofen), D-[5-(2-chloro-$\alpha,\alpha,\alpha$-trifluoro-p-tolyloxy)-2-nitrobenzoyl] glycolic acid (fluroglycofen) or salts or ester thereof, 2,4-dichlorophenyl-4-nitrophenyl ether (nitrofen), methyl-(2,4-dichlorophenoxy)-2-nitrobenzoate (befenox), 2-nitro-5-(2-chloro-4-trifluoromethyl-phenoxy) benzoic acid (aciflurofen) and salts and esters thereof, 2-chloro-4-trifluormethylphenyl 3-ethoxy- 4-nitrophenyl ether (oxyfluorfen) and 5-(2-chloro-4-(trifluoromethyl)phenoxy)-N-(methylsulfonyl)-2-nitrobenzamide (fomesafen); 2,4,6-trichlorophenyl 4-nitrophenyl ether (chlornitrofen) and 5-(2,4-dichlorophenoxy)-2-nitroanisole (chlomethoxyfen);

S. phenoxyphenoxypropionate herbicides such as (RS)-2-[4-(2,4-dichloro-phenoxy)phenoxy) propionic acid (diclofop) and esters thereof such as the methyl ester, 2-(4-(5-trifluoromethyl)-2-(pyridinyl)oxy]phenoxypropanoic acid (fluazifop) and esters thereof, 2-(4-(3-chloro-5-trifluoro-methyl)-2-pyridinyl)oxy)phenoxy)-propanoic acid (haloxyfop) and esters thereof, 2-(4-((6-chloro-2-quinoxalinyl)oxy)phenoxypropanoic acid (quizalofop) and esters thereof and ($\pm$)-2-[4-(6-chlorobenzoxazol-2-yloxy)phenoxy]propionic acid (fenoxaprop) and esters thereof such as the ethyl ester;

T. cyclohexanedione herbicides such as 2,2-dimethyl -4,6-dioxo-5-(1-((2-propenyloxy)imino)butyl) cyclohexane carboxylic acid (alloxydim) and salts thereof, 2-(1-ethoxyimino) butyl-5-(2-(ethylthio)-propyl)-3-hydroxy -2-cyclohexan-1-one(sethoxydim), 2-(1-ethoxyimino) butyl)-3-hydroxy-5-thian-3-ylcyclohex-2-enone (cycloxydim) 2-[1-(ethoxyimino)propyl]-3-hydroxy -5-mesitylcyclohex-2-enone(tralkoxydim), and ($\pm$) -2-(E)-1-[(E)-3-chloroallyloximino]propyl -5-[2-(ethylthio)propyl]-3-hydroxy-cyclohex-2-enone (clethodim);

U. sulfonyl urea herbicides such as 2-chloro-N (4-methoxy-6-methyl-1,3,5-triazin-2-yl)aminocarbonyl) benzenesulphonamide (chlorosulfuron), methyl 2-((((4,6-dimethyl-2-pyrimidinyl)amino)carbonyl)amino)-sulphonylbenzoic acid (sulfometuron), 2-(((3-(4-methoxy-6-methyl-1,3,5-triazin-2-yl)carbonyl) amino)-sulphonyl)benzoic acid (metsulfuron) and esters thereof; -(4,6-dimethoxypyrimidin-2-ylcarbamoylsuphamoyl)-O-toluic acid (benzsulfuron) and esters thereof such as the methyl 3-[3-(4-methoxy-6methyl-1,3,5-triazin-2-yl)ureidosulphonyl]thiophene-2-carboxylate (DPX-M6313), 2-(4-chloro-6-methoxy pyrimidin-2-yl carbamoylsulphamoyl benzoic acid (chlorimuron) and esters such as the ethyl ester thereof 2-(4,6-dimethoxypyrimidin-2-ylcarbamoylsulphamoyl)-N, N-dimethylnicotinamide, 2-[4,6-bis(difluoromethoxy) pyrimidin-2-ylcarbamoylsulphamoyl]benzoic acid (pirimisulfuron) and esters such as the methyl ester thereof, 2-[3-(4-methoxy-6-methyl-1,3,5-triazin-zyl)-3-methylureidosulphonyl] benzoic acid esters such as the methyl ester thereof (DPX-LS300) and 5-(4,6-dimethoxypyrimidin-2-ylcarbamoylsulphamoyl)-1-methyl-pyrazole-4-carboxylic acid (pyrazosulfuron);

V. imidazolidinone herbicides such as 2-(4,5-dihydro-4-isopropyl-4-methyl-5-oxoimidazol-2-yl) quinoline-3-carboxylic acid (imazaquin), methyl 6-(4-isopropyl-4-methyl-5-oxo-2-imidazolin-2-yl) -m-toluate and p-toluate isomer(imazamethabenz), 2-(4-isopropyl-4-methyl-5-oxo-2-imidazolin-2-yl) nicotinic acid (imazapyr) and isopropylammonium salts thereof, (RS)-5-ethyl-2-(4-isopropyl)-4-methyl-5-oxo-2-imidazolin-2-yl)nicotinic acid (imazethapyr);

W. arylanilide herbicides such as benzoyl-N-(3-chloro-4-fluorophenyl)-L-alanine (flamprop) and esters thereof, ethyl N-benzoyl-N-(3,4-dichlorophenyl)-DL-alaninate (benzoylprop -ethyl), N-(2,4-difluorophenyl)-2-(3-trifluoromethyl)phenoxy)-3-pyridinecarboxamide (diflufenican); and X. amino acid herbicides such as N-(phosphonomethyl)-glycine (glyphosate) and DL-homoalanin-4-yl(methyl)-phosphinic acid (phosphinothricin) and their salts and esters, trimethylsulfonium N-(phosphonomethyl)-glycine (sulphosate), and bilanafos;

Y. organoarsenical herbicides such as monosodium methanearsonate (MSMA);

Z. herbicidal amide derivative such as (RS)-N,N-diethyl-2-(1-naphthyloxypropionamide) (napropamide), 3,5-dichloro-N-(1,1-dimethylpropynyl)benzamide (propyzamide), (R)-1-(ethylcarbamoyl)ethyl carbanilate (carbetamide), N-benzyl-N- isopropylpivalamide (tebutam), (RS)-2-bromo- N-(1,1-dimethylbutyzamide (bromobutide), N-[3-(1-ethyl-1-methylpropyl)-isoxazol-5-yl] 2,6-dimethoxybenzamide, (isoxaben), N-phenyl-2-(2-naphthyloxy) propionamide (naproanilide), N,N -dimethyl-diphenylacetamide (diphenamid), and N-(1-naphthyl)-phthalamic acid (naptalam);

AA. miscellaneous herbicides including 2-ethoxy-2,3-dihydro-3, 3-dimethylbenzofuran methanesulfonate (ethofumesate), 7-oxabicyclo (2.2.1)heptane,1-methyl-4-(1-methylethyl)-2-(2-methylphenylmethoxy) -exo (cinmethylin), 1,2-dimethyl-3,5-diphenylpyrazolium ion (difenzoquat) and salts thereof such as the methyl sulphate salt, 2-(2-chlorobenzyl)-4,4-dimethyl-1,2-oxazoldin -3-one (clomazone), 5-tert-butyl-3-(2,4-dichloro-5-isopropoxyphenyl)-1,3,4-oxadiazol-2(3H)-one (oxadiazon), 3,5-dibromo-4-hydroxy benzaldehyde 2,4-dinitrophenyloxime (bromofenoxim), 4-chlorobut-2-ynyl-3-chlorocarbanilate (barban), (RS)-2-(3,5-dichlorophenyl)-2-(2,2, 2-trichloroethyl)oxirane (tridiphane), (3RS,4RS; 3RS,4SR)-3-chloro-4-chloromethyl-1-(α,α,α-trifluro-m-totyl)-2-pyrrolidone (in the ratio 3:1) (fluorodichloridone), dichloroquinoline 8-carboxylic acid (quinchlorac) and 2-(1,3-benzothiazol-2-yl- oxy)-N-methylacetanilide (mefanacet);

BB. Examples of useful contact herbicides include:
bipyridylium herbicides such as those in which the activity entity is the 1,1'-dimethyl-4,4'-dipyridylium ion (paraquat) and those in which the active entity is the 1,1'-ethylene-2,2'-dipyridylium ion (diquat);

The following examples are given by way of illustration only.

EXAMPLE 1

Preparation of 5-Bromo-2-(4-chlorophenyl) thiazol-4-yl-acetic acid (Compound No. 9 in Table 1)

Bromine (15.9 g, 5.15 ml, 0.1 mol) was added dropwise to 2-(4-chlorophenyl) thiazol-4-yl acetic acid (24 g, 0.096 mol) suspended in glacial acetic acid (200 ml) and the resulting mixture was heated at 60°-70° C. for 5 hours. The reaction mixture was cooled to 0° C. (ice bath) and the solid which separated was filtered and washed with $CHCl_3$. The residue was then washed with cold ethanol to afford the desired product (24 g, 75%)

'HNMR (DMSO-$d_6$) 3.75 (2H, S, $CH_2CO$) and 7.7 (4H, AB quartet, aromatic C-H)

EXAMPLE 2

Preparation of Methyl-5-bromo-2-(4-chlorophenyl thiazol-4-yl acetic ester (Compound No. 17 in Table 1)

The reaction as substantially described in Example 1 was carried out up to the cooling step. The solid which separated was filtered and washed with cold acetic acid. The crude 5-bromo-2-(4-chlorophenyl) thiazol-4-yl acetic acid without further purification was dissolved in hot methanol (100 ml) and the resulting reaction mixture heated under reflux for 20 mins (the esterification was monitored by silica TLC, eluting in $CH_2Cl_2$). The reaction mixture was allowed to cool to room temperature, and the solid which separated out of solution was filtered and air dried to yield the desired product.

$^1$H NMR ($CDCl_3$) 3.65 (3H, s, $OCH_3$), 3.8 (2H, s, $CH_2CO$) and 7.6 (4H, AB quartet, aromatic C—H).

EXAMPLE 3

Preparation of Ethyl-5-bromo-2-(4-chlorophenyl)thiazol-4-yl acetic ester (Compound No. 19 in Table 1)

5-Bromo-2-(4-chlorophenyl)thiazol-4-yl acetic acid, (prepared as described in Example 1 but without recrystallisation from ethanol) was dissolved in a mixture of hot ethanol (100 ml) and conc. $H_2SO_4$ (4 drops, 0.1 ml) and the resulting solution was heated under reflux for 40 min. The fraction mixture was allowed to cool to room temperature and the solid which separated out of solution was filtered, and washed with cold ethanol to yield the desired product (24.2 g, 71%) m.p. 75°-77° C., $^1$H NMR ($CDCl_3$) 1.3 (3H,t,$CH_2CH_3$) 3.9 (2H,s,$CH_2CO$) 4.25 (2H,q,$CH_2CH_3$), and 7.55 (4H,AB, quartet, aromatic C—H).

EXAMPLE 4

Preparation of n-Propyl-5-bromo-2-(4-chlorophenyl) thiazol-4-yl acetic ester (Compound No. 18 in Table 1)

5-Bromo-2-(4-chlorophenyl) thiazol-4-yl acetic acid (prepared as described in Example 1 but without recrystallisation from ethanol) was dissolved in a mixture of hot n-propanol (100 ml) and concentrated sulphuric acid (4 drops, 0.1 ml) and the resulting solution was heated under reflux for 6 hours. The reaction mixture was cooled to room temperature and poured into $H_2O$ (25 ml). The solution was neutralised ($NaHCO_3$), and the precipitate filtered to yield the desired product (1.33 g, 60%)

$^1$HNMR ($CDCl_3$) 0.95 (3H, t, $CH_2CH_2CH_2CH_3$), 1.35 (2H, hextet, $CH_2CH_2CH_2CH_3$), 1.6 (2H, quintet, $CH_2CH_2CH_2CH_3$), 3.9 (2H, S, $CH_2CO$), 4.15 (2H, t, $OCH_2CH_2CH_2CH_3$), and 7.6 (4H, AB quartet, aromatic C—H).

EXAMPLE 6

Preparation of 5-Chloro-2-(4-chlorophenyl) thiazol-4-yl acetic ester (Compound No. 4 in Table I)

Chlorine gas was bubbled through a stirred suspension of 2-(4-chlorophenyl) thiazol-4-yl acetic acid (10 g, 39 mmol) in glacical acetic acid (150 ml). After 1 min the thiozolylacetic acid had dissolved and after 2 min of bubbling a precipitate began to form. Chlorine was bubbled for a total of 20 min, and the reaction mixture allowed to stir for a further 30 minutes. The precipitate was filtered and air dried to afford the product (10.5 g, 93%).

$^1$H NMR (CDCl$_3$) 3.7 (2H, s, C$\underline{H}_2$CO), and 7.6 (4H, AB quartet, aromatic C—H).

EXAMPLE 7

Preparation of methyl-5-chloro-2-(4-chlorophenyl)thiazol-4-ylacetic ester (Compound Number 14 in Table I 5-Chloro-2-(4-chlorophenyl)thiazol-4-yl acetic acid (3.5 g, 12 mmol) prepared as described in Example 6, was dissolved in a solution of hot MeOH (50 ml) and concentrated. H$_2$SO$_4$ (0.1 ml) and the resulting reaction mixture heated under reflux for 4 hours. The reaction mixture was cooled to room temperature and poured into H$_2$O (50 ml). The solution was neutralized (NaHCO$_3$) and the precipitate formed filtered and air dried to afford the product (3.0 g, 83%).

$^1$H NMR (CDCl$_3$) 3.7 (3H, s, OCH$_3$), 3.8 (2H, s, CH$_2$CO), and 7.6 (4H, AB quartet, aromatic C—H).

EXAMPLE 8

Preparation of Ethyl-5-chloro-2-(4-chlorophenyl)thiazol-4-yl acetic ester (Compound No. 20 in Table I)

The reaction as descried in Example 7 was carried out using ethanol instead of methanol to give the desired product (3.0 g, 79%), $^1$HNMR (CDCl$_3$) 1.15 (3H, t, CH$_2$C$\underline{H}_3$), 3.8 (2H, s,CH$_2$CO), 4.1 (2H, q, C$\underline{H}_2$CH$_3$), and 7.6 (4H, AB quartet, aromatic C—H).

EXAMPLE 9

Preparation of n-Propyl-5-chloro-2-(4-chlorophenyl) thiazol-4-yl acetic ester (Compound No. 15 in Table I)

The reaction as described in Example 7 was carried out using n-propanol instead of methanol to give the desired product (3.0 g, 78%)

$^1$HNMR (CDCl$_3$) 0.95 (3H, t, CH$_2$CH$_2$C$\underline{H}_3$), 1.7 (2H, hextet, CH$_2$C$\underline{H}_2$CH$_3$), 3.85 (2H, s, C$\underline{H}_2$CO), 4.1 (2H, t, C$\underline{H}_2$CH$_2$CH$_3$), and 7.6 (4H, AB quartet, aromatic C—H).

EXAMPLE 10

Preparation of Ethyl-2-(4-bromophenyl)-5,6-dihydrocyclopentadienyl thiazol-4-yl-carboxylic ester (Compound No. 192 in Table II)

A mixture of 5-bromo-2-carbethoxycyclopentane (described by A. M. Khaletskii et al, Zhur Obshchei, Khm. 31, 737 (1961); 7 g 29.9 mmol] and 4-bromothiobenzamide (3 g, 14 mmol) were heated under reflux in ethanol (70 ml) for 6 hours. The reaction mixture was cooled to room temperature and concentrated under reduced pressure. The residue was dissolved in ethyl acetate washed consecutively with aqueous NaOH (10%), brine, H$_2$O, dried (MgSO$_4$) filtered and concentrated under reduced pressure. The product was purified by flash chromatography (eluting with 10% ethyl acetate/Hexane) to afford the desired product (1.6 g, 33%).

$^1$HNMR (CDCl$_3$) 1.30 (3H, t, OCH$_2$C$\underline{H}_3$), 2.82 (2H, m, CH$_2$CO), 3.00 (1H, m,

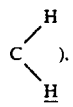

3.15 (1H, m,

4.04 (1H, t, C$\underline{H}_2$CO$_2$CH$_2$CH$_3$), 4.22 (2H. q. OC$\underline{H}_2$CH$_3$), and 7.6 (4H, AB quartet, aromatic C—H).

EXAMPLE 11

Preparation of Ethyl-2-phenyl-5,6-dihydrocyclopentadienylthiazol-4-yl carboxylic ester (Compound No. 183 in Table II)

A mixture of 5-bromo-2-carbethoxycyclopentane (14.5 g, 0.62 mmol) and thiobenzamide (7 g, 0.05 mmol) were heated under reflux in toluene (75 ml) for 90 minutes. The toluene solution was decanted from the oil residue and organic layer washed with sodium bicarbonate solution, water, dried (MgSO$_4$), filtered and concentrated under reduced pressure. The product (0.99 g, 6.5%) was purified by flash chromatography (eluting with 15% EtOAc/hexane).

$^1$H NMR (CDCl$_3$) 1.28 (3H,t, OCH$_2$C$\underline{H}_3$), 2.8 (2H,t, ring CH$_2$), 2.98 and 3.10 (1H, m, ring C$\underline{H}_2$), 4.04 (1H, t, C$\underline{H}$ CO$_2$Et), 4.22 (2H, q., OC$\underline{H}_2$CH$_3$) and 7.6 (4H, AB quartet, aromatic C—H).

EXAMPLE 12

Preparation of Ethyl-2-(4-t-butylphenyl)-5,6-dihydrocyclopentadienylthiazol-4-ylcarboxylic ester (Compound No 184 in Table II)

The reaction as described in Example 11 was carried out using 4-t-butylthiobenzamide (6.0 g, 0.03 mol) instead of thiobenzamide to give the desired product (1.72 g, 17.5%).

$^1$H NMR (CDCl$_3$) 1.32 (12H, m, $^t$Bu and OCH$_2$C$\underline{H}_3$), 2.9 (4H, m, ring H), 4.04 (1H, t, C$\underline{H}$—CO$_2$Et), 4.24 (2H, q, OC$\underline{H}_2$CH$_3$), and 7.6 (4H, AB quartet, aromatic C—H).

EXAMPLE 13

Preparation of Ethyl-2-(4-trifluoromethylbenzene)-5,6-dihydrocyclopentadienylthiazol-4-yl-carboxylic ester (Compound No. 185 in Table II)

The reaction as described in Example 10 was carried out using 4-trifluorothiobenzamide (6.0 g, 0.29 mol) instead of 4-bromothiobenzamide to give the desired product (2.47 g, 25%).

$^1$H NMR (CDCl$_3$) 1.30 (3H, t, OCH$_2$C$\underline{H}_3$), 2.82 (2H, m, ring CH$_2$), 2.98 and 3.15 (2H, m, ring C$\underline{H}_2$), 4.05 (1H, t, C$\underline{H}$ CO$_2$Et), 4.25 (2H, q, OC$\underline{H}_2$CH$_3$), and 7.85 (4H, AB quartet, aromatic C—H).

EXAMPLE 14

Preparation of Ethyl-2-(3-chloro-4-fluorophenyl)-5,6-dihydrocyclopentadienylthiazol-4-ylcarboxylic ester. (Compound No. 188 in Table II)

The reaction as described in Example 10 was carried out using 3-chloro-4-fluorothiobenzamide (5 g, 26 mmol) instead of 4-bromothiobenzamide to give the desired product (2.55 g, 29%).

$^1$H NMR (CDCl$_3$) 1.31 (3H, t, OCH$_2$CH$_3$), 2.83 (2H, m, ring CH$_2$), 3.0 and 3.10 (2H, m, ring CH$_2$), 4.03 (1H, t, CH CO$_2$Et), 4.23 (2H, q, OCH$_2$ CH$_3$), 7.17 (1H, t, aromatic C—H), 7.74 (1H, m, aromatic C—H), and 7.99 (1H, d, aromatic C—H).

EXAMPLE 15

Preparation of Ethyl-2-(4-fluorophenyl)-5,6-dihydrocyclopentadienyl thiazol-4-yl-carboxylic ester. (Compound No. 197 in Table II)

The reaction as described in Example 10 was carried out using 4-fluorothiobenzamide instead of 4-bromothiobenzamide to give the desired product (2.19 g, 29%).

$^1$H NMR (CDCl$_3$) 1.3 (3H, t, OCH$_2$CH$_3$), 2.8 (2H, t, ring CH$_2$), 2.9 and 3.1 (2H, m, ring CH$_2$), 4.0 (1H, t, CH CO$_2$Et), 4.2 (2H, q, OCH$_2$ CH$_3$), and 7.5 (4H, AB quartet, aromatic C—H),

EXAMPLE 16

Preparation of Compound No. 59 in Table I

Bromine (3 ml, 58 mmol) was added dropwise (2 min) to ethyl-2-isopropylacetoacetate (10.4 ml 58 mmol) in ether (20 ml) at 0° C. (ice bath) and the resulting mixture stirred for a further 20 minutes. The reaction mixture was concentrated under reduced pressure and the residue was dissolved in EtOH (70 ml), 4-chlorothiobenzamide (5.1 g) was added and the resulting solution refluxed for 5 hours. The reaction mixture was cooled, and concentrated under reduced pressure. The residue was partitioned between 10% NaOH and EtOAc, and the organic layer dried (MgSO$_4$), filtered and concentrated in vacuo. The product (3.7 g, 38%) was purified by flash chromatography (eluted with 10% EtOAc/hexane).

$^1$H NMR (CDCl$_3$) 0.9 [3H, d, CH(CH$_3$)$_2$], 1.05 (3H, d, CH(CH$_3$)$_2$), 1.26 (3H, t, OCH$_2$CH$_3$), 2.45 (1H, m, CH(CH$_3$)$_2$), 3.70 (1H, d, CHCO$_2$Et), 4.18 (2H, m, OCH$_2$CH$_3$), 7.25 (1H, s, thiazole ring H), and 7.6 (4H, AB, aromatic C—H).

EXAMPLE 17

Preparation of Compound No. 60 in Table I

Bromine (0.5 ml, 9.7 mmol) in acetic acid (4.5 ml) was added dropwise to compound 59 (3.16 g 9.7 mmol) in acetic acid (30 ml) and the resulting mixture was heated at 90° C. for 14 hours. The reaction mixture was cooled, then poured in saturated sodium bicarbonate solution and neutralised. The oil was extracted onto chloroform (3×) and the combined organic extracts dried (MgSO$_4$), filtered and concentrated under reduced pressure. The product was purified by flash chromatography (eluted with 2% EtOAc/Hexane) (0.9 g, 25%).

$^1$H NMR (CDCl$_3$) 0.85 (3H, d, CH(CH$_3$)$_2$), 1.10 (3H, d, CH(CH$_3$)$_2$), 1.25 (3H, t, OCH$_2$CH$_3$), 2.72 (1H, m, CH(CH$_3$)$_2$), 3.68 (1H, d, CHCO$_2$Et), 4.16 (2H, q, OCH$_2$CH$_3$), and 7.55 (4H, AB quartet, aromatic C—H).

EXAMPLE 18

Preparation of Compound No. 61 in Table I

NaH (0.8 g, 50% oil dispersion, 1.05 equiv) was added to compound 20 (5g, 15.8 mmol) dissolved in dry dimethoxyethane (DME) (35 ml) and the resulting mixture stirred for 10 minutes at room temperature. Iodomethane (1.2 equiv) was added dropwise, and the resulting mixture was stirred for a further 2 hours. Water was added and the solution was extracted with chloroform (3×). The combined organic extracts were dried (MgSO$_4$), filtered, and concentrated under reduced pressure. The product was purified by chromatography (6% EtOAc/Hexane) (2.63 g, 50%).

$^1$HMR (CDCl$_3$) 1.24 (3H, t, OCH$_2$CH$_3$), 1.60 (3H, d, CH(CH$_3$)CO$_2$Et), 4.05 (1H, q, CH(CH$_3$)CO$_2$Et) 4.17 (2H, q, OCH$_2$, CH$_3$), and 7.5 (4H, AB quartet, aromatic C—H).

EXAMPLE 19

Preparation of N,N-Dimethyl-5-chloro-2-phenylthiazol-4-yl-acetamide (Compound No. 28 in Table I)

A mixture of 5-chloro-2-phenylthiazol-4-yl-acetic acid (1.98 g, 7.8 mmol), tetramethylsulphurous diamide (1.01 g, 9 mmol) and chloroform (dry, 30 ml) were heated under reflux for 4 hours. The reaction mixture was cooled and was concentrated under reduced pressure. The residue was taken up into chloroform (100 ml) and H$_2$O (50 nl) and an excess of sodium bicarbonate added. After filtration the chloroform layer was washed with dilute HCl, water, dried (MgSO$_4$), filtered and was concentrated under reduced pressure. The product was purified from hot petroleum ether (100°–126° C.) (0.47 g) m.p. 77°–79° C.

Microanalysis C: 55.62, H: 4.04; N: 9.98 (expected C: 55.55; H: 4.77; N: 9.97).

EXAMPLE 20

Preparation of N,N-Dimethyl-5-chloro-2-(4-chlorophenyl)thiazol-4-yl-acetamide (Compound No. 62 in Table I)

A mixture of 5-chloro-2-(4-chlorophenyl)thiazol-4-yl-acetic acid (19.1 g, 64 mmol), thionyl chloride (1.2 equiv., 48 ml 77 mmol), and chloroform were heated at 80° C. for 1 hour. The reaction mixture was cooled and then concentrated under reduced pressure. The residue was dissolved in chloroform (200 ml) then saturated with dimethylamine (gas). The reaction mixture was heated under reflux for 2 hours, and concentrated under reduced pressure. The product was purified by flash chromatography (eluted with 70% EtOAc/Hexane) (14.0 g, 66%).

$^1$H NMR (CDCl$_3$) 3.0 (3H, s, N(CH$_3$)$_2$), 3.2 (3H, s, N(CH$_3$)$_2$), 3.9 (2H, s, CH$_2$CON(CH$_3$)$_2$), and 7.6 (4H, AB quartet, aromatic C—H).

EXAMPLE 21

Preparation of N,N-Dimethyl-5-chloro-2-(4-chlorophenyl)thiazol-4-yl-acetohydrazide. (Compound No. 63 in Table I)

The reaction as described in Example 20 was carried out using N,N-dimethylhydrazine (1.16 ml) instead to dimethylamine to give the desired product.

$^1$H NMR (CDCl$_3$) 3.2 (6H, s, NHN(CH$_3$)$_2$), 3.8 (2H, s, CH$_2$CONHN(CH$_3$)$_2$), 7.6 (4H, AB quartet, aromatic C—H) and 12.8 (1H, bs, NHN(CH$_3$)$_2$).

EXAMPLE 22

Preparation of N-Butyl-5-bromo-2-(4-chlorophenyl)thiazol-4-ylacetic ester. (Compound No. 64 in Table 1)

The reaction as described in Example 7 was carried out using n-Butanol and refluxing for 9 hours instead of methanol and refluxing for 4 hours to give the desired product (1.1 g, 47%).

$^1$H NMR (CDCl$_3$) 0.9 (3H, t, CH$_3$), 1.35 (2H, s, OCH$_2$CH$_2$CH$_2$CH$_3$), 1.6 (2H, s, OCH$_3$2CH$_2$CH$_2$CH$_3$), 3.8 (2H, s, CH$_2$CO), and 7.6 (4H, AB quartet, aromatic C—H).

EXAMPLE 23

Preparation of Methylsulphonyl-5-chloro-2-(4-chlorophenyl)thiazol-4-yl-acetamide. (Compound No. 68 in Table I)

The reaction as described in Example 20 was carried out using methylsulphonamide (1.45 g, 15.2 mmol) and 14 hours refluxing in place of dimethylamine and 2 hours refluxing. The precipitate was isolated by suction, washed with boiling MeOH, to give the desired product (0.7 g).

$^1$H NMR (CDCl$_3$) 3.2 (3H, s, NHSO$_2$Me), 3.8 (2H, s, CH$_2$CO), 7.7 (4H, AB quartet, aromatic C—H) and 12.1 (1H, bs, NHSO$_2$Me).

EXAMPLE 24

Preparation of N-Phenyl-5-bromo-2-(4-chlorophenyl)thiazol-4-yl-acetamide. (Compound No. 69 in Table I)

A mixture of 5-bromo-2-(4-chlorophenyl)thiazol-4-yl-acetic acid (1 g, 3 mmol), thionyl chloride (2 equiv., 0.72 g, 6 mmol), and chloroform were heated under reflux for 2.5 hours. The reaction mixture was cooled and concentrated under reduced pressure. The residue was dissolved in CHCl$_3$ (dry), followed by dropwise addition of aniline (2 equiv., 0.56 g, 6 mmol) and the resulting mixture refluxed for a further 5 hours. The reaction mixture cooled to room temperature and the precipitate was collected by filtration. The filtrate was concentrated under reduced pressure. The residue was triturated with EtOAc, and filtered to yield the desired product (0.4 g, 32%).

$^1$ HNMR (CDCl$_3$) 3.8 (2H, s, CH$_2$CONHC$_6$H$_5$), 7.0 (1H, dd, NHC$_6$H$_5$), 7.2 (2H, dd, NHC$_6$H$_5$), 7.6 (2H, d, NHC$_6$H$_5$), 7.4 (4H, AB quartet, aromatic C—H), and 10.2 (1H, s, HNC$_6$H$_5$).

EXAMPLE 25

Preparation of Ethyl-2-(4-iodophenyl)thiazol-4-yl acetic ester. (Compound No. 67 in Table I)

A mixture of 4-iodothiobenzamide (4.6 g, 17.7 mmol), toluene (dry 120 ml), pTsOH (cat., 20 mg), and ethyl-4-bromoacetoacetate were heated under reflux in a Dean and Stark apparatus for 4 hours. The reaction mixture was cooled and concentrated under reduced pressure, and the product purified by chromatography (eluted with 25% EtOAc/petrol; 2.6 g, 39%).

$^1$H NMR (CDCl$_3$) 1.3 (3H, t, OCH$_2$CH$_3$), 3.9 (2H, s, CH$_2$COCH$_2$CH$_3$), 4.2 (2H, q, OCH$_2$CH$_3$), and 7.2 (1H, s, thiazolyl ring H), and 7.75 (4H, AB quartet, aromatic C—H).

EXAMPLE 26

Preparation of Ethyl-5-bromo-2-(4-iodophenyl)thiazol-4-ylacetic ester. (Compound No. 70 in Table I)

The reaction described in Example 1 was repeated using ethyl-2-(4-iodophenyl)thiazol-4-yl acetic ester (0.83 g) in place of 2-(4-chlorophenyl)thiazol-4-yl acetic acid to yield the desired product (0.3 g).

$^1$ NMR (CDCl$_3$) 1.15 (3H, t, OCH$_2$CH$_3$), 3.8 (2H, s, CH$_2$CO$_2$Et), 4.05 (2H, q, OCH$_2$CH$_3$), and 7.7 (4H, AB quartet, aromatic C—H).

EXAMPLE 27

Preparation 2-Hydroxyethyl-5-bromo-2-(4-chlorophenyl)thiazol-4-yl acetic ester. (Compound No. 72 in Table I)

The reaction described in Example 4 was repeated using ethyleneglycol (10 ml, excess) in place of n-propanol to yield the desired product (0.52 g, 46%).

$^1$H NMR (CDCl$_3$) 3.8 (2H, t, OCH$_2$CH$_2$OH), 3.9 (2H, s, CH$_2$CO), 4.3 (2H, t, OCH$_2$CH$_2$OH), and 7.6 (4H, AB quartet, aromatic C—H).

EXAMPLE 28

Preparation of 2-Methoxyethyl-5-bromo-2-(4-chlorophenyl)thiazol-4-yl acetic ester. (Compound No. 71 in Table I)

The reaction described in Example 4 was repeated using 2-methoxyethanol, (10 ml) in place of n-propanol to yield the desired product (0.4 g, 23%).

$^1$H NMR (CDCl$_3$) 3.4 (3H, s, OCH$_2$CH$_2$OMe), 3.6 (2H, t, OCH$_2$CH$_2$OMe), 3.9 (2H, s, CH$_2$CO), 4.3 (2H, t, OCH$_2$CH$_2$OMe), and 7.6 (4H, AB quartet, aromatic C—H).

EXAMPLE 29

Preparation of 3-Methylbutyl-5-chloro-2-(4-chlorophenyl)thiazol-4-yl acetic ester. (Compound No. 73 in Table I)

Dicyclohexylcarbodimide (DCC) (1.1 equiv., 0.76 g 3.8 mmol) in CHCl$_3$ was added dropwise to 3-methyl-butanol (2 equiv., 0.61 g, 7.0 mmol), DMAP (cat., 40 mg), and 5-chloro-2-(4-chlorophenyl)thiazol-4-yl acetic acid (1 g, 3.5 mmol) suspended in CH$_2$Cl$_2$ (dry, 20 ml) at 0° (ice bath) and the resulting mixture stirred for 20 minutes. The reaction mixture was stirred for a further 2 hours at room temperature, then concentrated under reduced pressure. The product was purified by flash chromatography (eluted in 10% EtOAc/Hexane) (0.5 g).

$^1$H NMR (CDCl$_3$) 0.9 (6H, d, CH(CH$_3$)$_2$), 1.55 (2H, q, CH$_2$CH$_2$CH(CH$_3$)$_2$), 1.7 (1H, m, CH(CH$_3$)$_2$), 4.2 (2H, t, COCH$_2$CH$_2$), and 7.6 (4H, A quartet, aromatic C—H).

EXAMPLE 30

Preparation of Allyl-5-chloro-2(4-chlorophenyl)thiazol-4-yl-acetic ester. (Compound No. 74 in Table I)

The reaction as described in Example 29 was carried out using allyl alcohol (2 equiv., 0.4 g, 6.9 mmol) in place of 3-methylbutanol to give the desired product (350 mg, 27%).

$^1$H NMR (CDCl$_3$) 3.95 (2H, s, C$\underline{H}_2$CO), 4.55 (2H, d, OC$\underline{H}_2$CH=CH$_2$), 5.3 (2H, m, OCH$_2$CH=C$\underline{H}_2$), 5.95 (1H, m, OCH$_2$C$\underline{H}$=CH$_2$), and 7.6 (4H, AB quartet, aromatic C—H).

EXAMPLE 31

Preparation of 3-Pentyl-5-chloro-2(4-chlorophenyl)thiazol-4-yl-acetic ester. (Compound No. 75 in Table I)

The reaction as described in Example 29 was carried out using 3-pentanol (2 equiv., 0.612 g, 6.9 mmol) in place of 3-methylbutanol to give the desired product (250 mg, 25%).

$^1$H NMR (CDCl$_3$) 0.75 (6H, t, CH(CH$_2$C$\underline{H}_3$)$_2$), 1.45 (4H, m, CH(C$\underline{H}_2$CH$_3$)$_2$), 3.8 (2H, s, C$\underline{H}_2$CO), 4.65 (1H, p, C$\underline{H}$(CH$_2$CH$_3$)$_2$), and 7.7 (4H, AB quartet, aromatic C—H).

EXAMPLE 32

Preparation of Propargyl-5-chloro-2-(4-chlorophenyl)thiazol-4-yl-acetic ester. (Compound No. 76 in Table I)

The reaction as described in Example 29 was carried out using propargyl alcohol (2 equiv., 0.38, 6.9 mmol) in place of 3-methylbutanol to give the desired product (360 mg).

$^1$H NMR (CDCl$_3$) 1.5 (1H, s, CH$_2$C C$\underline{H}$), 3.9 (2H, s, C$\underline{H}_2$CO), 4.75 (2H, s, C$\underline{H}_2$C CH), and 7.6 (4H, AB quartet, aromatic C—H).

EXAMPLE 33

Preparation of N-Pentyl-5-chloro-2-(4-chlorophenyl)thiazol-4-yl-acetic ester. (Compound No. 77 in Table I)

The reaction described in Example 29 was carried out using n-pentanol (2 equiv., 0.612 g, 6.9 mmol) in place of 3-methylbutanol to give the desired product (0.5 g, 41%).

$^1$H NMR (CDCl$_3$) 0.9 (3H, d, CH$_2$C$\underline{H}_3$), 1.5-1.7 (6H, m, aliphatic H), 3.05 (3H, d, C$\underline{H}_2$CO), 4.2 (2H, t, OC$\underline{H}_2$), and 7.6 (4H, AB quartet, aromatic C—H).

EXAMPLE 34

Preparation of 3,7-Dimethyloctyl-5-chloro-2-(4-chlorophenyl)thiazol-4-yl acetic ester. (Compound No. 78 in Table I)

The reaction as described in Example 29 was carried out using 3,7 dimethyloctanol to give the desired product (540 mg).

$^1$H NMR (CDCl$_3$) 0.85-1.7 (19H, m, aliphatic H), 3.8 (2H, s, C$\underline{H}_2$CO), 4.2 (2H, t, OC$\underline{H}_2$) and 7.6 (4H, AB quartet, aromatic C—H).

EXAMPLE 35

Preparation of 2-Benzyloxyethyl-5-chloro-2-(4-chlorophenyl)thiazol-4-yl acetic ester. (Compound No. 79 in Table I)

The reaction as described in Example 29 was carried out using 2-benzyloxyethanol (2 equiv., 1.1 g, 6.9 mmol) in place of 3-methylbutanol to give the desired product (150 mg).

$^1$H NMR (CDCl$_3$) 3.65 (2H, t, OCH$_2$C$\underline{H}_2$O), 3.9 (2H, s, C$\underline{H}_2$CO), 4.35 (2H, t, OC$\underline{H}_2$CH$_2$O), 4.5 (2H, s, CH$_2$C$\underline{H}_2$OCH$_2$C$_6$H$_5$), 7.35 (m, aromatic C—H), and 7.5 (4H, AB quartet, aromatic C—H).

EXAMPLE 36

Preparation of Neopentyl-5-chloro-2-(4-chlorophenyl)thiazol-4-yl-acetic ester. (Compound No. 80 in Table I)

The reaction as described in Example 29 was carried out using neopentyl alcohol (2 equiv., 0.636 g, 6.9 mmol) in place of 3-methylbutanol to give the desired product (0.32 g).

$^1$H NMR (CDCl$_3$) 0.9 (9H, s, (C$\underline{H}_3$)$_3$), 3.84 (2H, s, C$\underline{H}_2$CO), 3.88 (2H, s, OC$\underline{H}_2$C(CH$_3$)$_3$, and 7.6 (4H, AB quartet, aromatic C—H).

EXAMPLE 37

Preparation of 2-Methylpropyl-5-chloro-2-(4-chlorophenyl)thiazol-4-yl acetic ester. (Compound No. 81 in Table I)

The reaction as described in Example 29 was carried out using 2-methylpropanol (0.53 g, 6.9 mmol), in place of 3-methylbutanol to give the desired product (0.46 g).

$^1$H NMR (CDCl$_3$) 0.9 (6H, d, CH(C$\underline{H}_3$)$_2$), 1.95 (1H, septet, C$\underline{H}$(CH$_3$)$_2$), 3.85 (2H, s, C$\underline{H}_2$CO) 3.95 (2H, d, OC$\underline{H}_2$), and 7.6 (4H, AB quartet, aromatic C—H).

EXAMPLE 38

Preparation of 2-Methylbutyl-5-chloro-2-(4-chlorophenyl)thiazol-4-yl-acetic ester. (Compound No. 82 in Table I)

The reaction as described in Example 29 was carried out using 2-methylbutanol (0.63 g, 6.9 mmol) in place of 3-methylbutanol to give the desired product (0.5 g).

$^1$H NMR (CDCl$_3$) 0.9 (6H, d, CHC$\underline{H}_3$), 1.2 (1H, m, C$\underline{H}$CH$_3$), 1.4-1.7 (3H, m, aliphatic $\underline{H}$), 3.8 (2H, s, C$\underline{H}_2$CO), 4.0 (2H, m, OC$\underline{H}_2$), and (4H, AB quartet, aromatic C—H).

EXAMPLE 39

Preparation of 1-Methylbutyl-5-chloro-2-(4-chlorophenyl)thiazol-4-yl-acetic ester. (Compound No. 83 in Table I)

The reaction as described in Example 29 was carried out using 1-methylbutanol (0.636 g, 6.9 mmol) in place of 3-methylbutanol to give the desired product (0.4 g).

$^1$H NMR (CDCl$_3$) 0.9 (3H, t, CH$_2$C$\underline{H}_3$), 1.25 (3H, d, CHC$\underline{H}_3$), 1.5 (4H, m, C$\underline{H}_2$C$\underline{H}_2$CH$_3$), 3.8 (2H, s, C$\underline{H}_2$CO), 5.0 (1H, sextet, O—C$\underline{H}$(CH$_3$)CH$_2$), and 7.6 (4H, AB quartet, aromatic C—H).

EXAMPLE 40

Preparation of 2,3-Dimethylpropyl-5-chloro-2-(4-chlorophenyl)-thiazol-4-yl acetic ester. (Compound No. 84 in Table I)

The reaction as described in Example 29 was carried out using 2,3-dimethylpropanol (0.61 g, 6.9 mmol) in place of 3-methylbutanol to give the desired product (0.36 g).

$^1$H NMR (CDCl$_3$) 0.9 (6H, d, CH(C$\underline{H}_3$)$_2$), 1.2 (3H, d, CHC$\underline{H}_3$), 1.8 (1H, sextet, C$\underline{H}$(CH$_3$)$_2$), 3.8 (2H, s, C$\underline{H}_2$CO), 4.9 (1H, sextet, OC$\underline{H}$(CH$_3$)$_2$), and 7.6 (4H, AB quartet, aromatic C—H).

EXAMPLE 41

Preparation of
1-Methylpropyl-5-chloro-2-(4-chlorophenyl)thiazol-4-yl acetic ester. (Compound No. 85 in Table I)

The reaction as described in Example 7 was carried out using 1-methylpropanol (0.517 g, 6.9 mmol) in place of 3-methylbutanol to give the desired product (0.34 g).

$^1$H NMR (CDCl$_3$) 0.9 (3H, t, CH$_2$C$\underline{H}_3$), 1.25 (3H, d, CH(C$\underline{H}_3$)), 1.6 (2H, sextet, CH(CH$_3$)C$\underline{H}_2$CH$_3$)) 3.8 (2H, s, C$\underline{H}_2$CO)), 4.9 (1H, sextet, C$\underline{H}$(CH$_3$), and 7.6 (4H, AB quartet, aromatic C—H).

EXAMPLE 42

Preparation of
Cyclohexylmethyl-5-chloro-2-(4-chlorophenyl)thiazol-4-yl acetic ester. (Compound No. 86 in Table I)

The reaction as described in Example 29 was carried out using cyclohexanemethanol (0.79 g, 6.9 mmol) in place of 3-methylbutanol to give the desired product (0.45 g).

$^1$H NMR (CDCl$_3$) 0.9–1.7 (11H, m, cyclohexane C—H), 3.8 (2H, s, C$\underline{H}_2$CO), 4.0 (2H, d, OC$\underline{H}_2$), and 7.6 (4H, AB quartet, aromatic C—H).

EXAMPLE 43

Preparation of
2-Methoxyisopropyl-2-chloro-2-(4-chlorophenyl) thiazol-4-yl acetic ester. (Compound No. 87 in Table I)

The reaction as described in Example 29 was carried out using 2-methoxyisopropanol (0.63 g, 6.9 mmol) in place of 3-methylbutanol to give the desired product (0.2 g).

$^1$H NMR (CDCl$_3$) 1.3 (3H, d, CHC$\underline{H}_3$), 3.35 (3H, s, OMe), 3.45 (2H, m, C$\underline{H}_2$OMe), 3.85 (2H, s, C$\underline{H}_2$CO), 5.15 (1H, sextet, OC$\underline{H}$(CH$_3$), and 7.6 (4H, AB quartet, aromatic C—H).

EXAMPLE 44

Preparation of
n-Hexyl-5-chloro-2(4-chlorophenyl)thiazol-4-yl-acetic ester. (Compound No. 88 in Table I)

The reaction as described in Example 29 was carried using n-hexanol (0.71 g, 6.9 mmol) in place of 3-methylbutanol to give the desired product (0.45 g).

$^1$H NMR (CDCl$_3$) 0.9 (3H, t, CH$_2$C$\underline{H}_3$), 1.3–1.6 (8H, m, aliphatic H), 3.8 (2H, s, C$\underline{H}_2$CO), 4.1 (2H, t, OC$\underline{H}_2$CH$_2$), and 7.6 (4H, AB quartet, aromatic C—H).

EXAMPLE 45

Preparation of
3-Methoxybutyl-5-chloro-2-(4-chlorophenyl) thiazol-4-yl acetic ester. (Compound No. 89 in Table I)

The reaction as described in Example 29 was carried out using 3-methoxybutanol (0.73 g, 6.9 mmol) in place of 3-methylbutanol to give the desired product (0.3 g).

$^1$H NMR (CDCl$_3$) 1.1 (3H,d,CHC$\underline{H}_3$), 1.8 (2H, m, CH$_2$CH(OMe)CH$_3$), 3.25 (3H, s, OC$\underline{H}_3$), 3.35 (1H, sextet, C$\underline{H}$(CH$_3$)), 3.8 (2H, s, C$\underline{H}_2$CO), 4.25 (2H, t, OC$\underline{H}_2$CH$_2$), and 7.6 (4H, AB quartet, aromatic C—H).

EXAMPLE 46

Preparation of
Benzyl-5-chloro-2-(4-chlorophenyl)thiazol-4-yl acetic ester. (Compound 90 in Table I)

The reaction as described in Example 29 was carried out using benzyl alcohol (0.75 g, 6.9 mmol) in place of 3-methylbutanol to give the desired product (0.49 g).

$^1$H NMR (CDCl$_3$) 3.9 (2H, s, C$\underline{H}_2$CO), 5.2 (2H, s, OC$\underline{H}_2$C$_6$H$_5$), 7.35 (5H, m, OCH$_2$C$_6$H$_5$), and 7.6. (4H, AB quartet, aromatic C—H).

EXAMPLE 47

Preparation of
p-Methoxyphenyl-5-chloro-2-(4-chlorophenyl)thiazol-4-yl acetic ester. (Compound No. 91 in Table I)

The reaction was described in Example 29 was carried out using p-methoxphenol (0.86 g, 6.9 mmol) in place of 3-methylbutanol to give the desired product (0.16 g).

$^1$H NMR CDCl$_3$ 3.8 (3H, s, OCH$_3$), 4.05 (2H, s, CH$_2$CO), 6.95 (4H, AB quartet, O—C$_6$$\underline{H}_4$OMe), and 7.6 (4H, AB quartet, aromatic C—H).

EXAMPLE 48

Preparation of
n-Octyl-5-chloro-2-(4-chlorophenyl)thiayol-4-yl acetic ester. (Compound No. 92 in Table I)

The reaction as described in Example 29 was carried out using n-octanol (0.9 g, 6.9 mmol) in place of 3-methylbutanol to give the desired product (0.57 g).

$^1$H NMR (CDCl$_3$) 0.9 (3H, t, CH$_2$C$\underline{H}_3$), 1.3–1.6 (12H, m, aliphatic C—H), 3.8 (2H, s, C$\underline{H}_2$CO), 4.15 (2H, t, OC$\underline{H}_2$CH$_2$), and 7.6 (4H, AB quartet, aromatic C—H).

EXAMPLE 49

Preparation of
p-Nitrophenyl-5-chloro-2-(4-chlorophenyl)thiazol-4-yl acetic ester. (Compound No. 93 in Table I)

The reaction as described in Example 29 was carried out using p-nitrophenol (0.96 g, 6.9 mmol) and refluxing for 4 hours in place of 3-methylbutanol and stirring at room temperature for 2 hours, to give the desired product (0.08 g).

$^1$H NMR (CDCl$_3$) 4.1 (2H, s, C$\underline{H}_2$CO), 7.6 (4H, AB quartet, aromatic C—H), and 7.8 (4H, AB quartet, O—C$_6$$\underline{H}_4$NO$_2$).

EXAMPLE 50

Preparation of
n-Decyl-5-chloro-2-(4-chlorophenyl)thiazol-4-yl acetic ester. (Compound No. 94 in Table I)

The reaction as described in Example 29 was carried out using n-decanol (2 equiv.), 1.1 g, 6.9 mmol) in place of 3-methylbutanol to give the desired product (0.59 g).

$^1$H NMR (CDCl$_3$) 0.9 (3H, t, CH$_2$C$\underline{H}_3$), 1.3–1.6 (16H, m, aliphatic C—H), 3.8 (2H, s, C$\underline{H}_2$CO), 4.15 (2H, t, OC$\underline{H}_2$CH$_2$), and 7.6 (4H, AB quartet, aromatic C—H).

EXAMPLE 51

Preparation of
Phenyl-5-chloro-2-(4-chlorophenyl)thiazol-4-yl acetic ester. (Compound No. 95 in Table I)

The reaction described in Example 29 was carried out using phenol (2 equiv. 0.51 g, 6.9 mmol) in place of 3-methylbutanol to give the desired product (0.07 g).

$^1$H NMR (CDCl$_3$) 4.1 (2H, s, C$\underline{H}_2$CO), 7.3 (5H, m, phenyl C—H), and 7.6 (4H, AB quartet, aromatic C—H).

EXAMPLE 52

Preparation of
Neopentyl-5-bromo-2-(4-chlorophenyl)thiazol-4-yl-acetic ester. (Compound No. 96 in Table I)

The reaction as described in Example 29 was carried out using 5-bromo-2-(4-chlorophenyl)thiazol-4-yl acetic acid (1 g, 3.0 mmol) and neopentanol (2 equiv, 0.53 g, 6 mmol) in place of 5-chloro-2-(4-chlorophenyl)thiazol-4-yl acetic acid and 3-methylbutanol to give the desired product (1.2 g).

$^1$H NMR (CDCl$_3$) 0.9 (9H, s, CH$_2$C(C$\underline{H}_3$)$_3$), 3.85 (2H, s, C$\underline{H}_2$CO), 3.9 (2H, s, C$\underline{H}_2$C(CH$_3$)$_3$), and 7.6 (4H, AB quartet, aromatic C—H).

EXAMPLE 53

Preparation of
2-Methoxyisopropyl-5-bromo-2-(4-chlorophenyl)-thiazol-4-yl acetic ester. (Compound No. 97 in Table I)

The reaction as described in Example 52 was carried out using 2-methoxyisopropanol (2 equiv., 0.54, 8.0 mmol) in place of neopentanol to give the desired product (0.15 g).

$^1$H NMR (CDCl$_3$) 1.2 (3H, d, CHC$\underline{H}_3$), 3.3 (3H, s, OC$\underline{H}_3$), 3.4 (2H, t, C$\underline{H}_2$OCH$_3$), 3.8 (2H, s, C$\underline{H}_2$CO), 5.1 (1H, m, OC$\underline{H}$CH$_3$), and 7.5 (4H, AB quartet, aromatic C—H).

EXAMPLE 54

Preparation of
Phenyl-5-bromo-2-(4-chlorophenyl)thiazol-4-yl-acetic ester. (Compound No. 98 in Table I)

The reaction as described in Example 52 was carried out using phenol (2 equiv, 0.56 g, 6.0 mmol) in place of neopentanol to give the desired product (0.13 g).

$^1$H NMR (CDCl$_3$) 4.1 (2H, s, C$\underline{H}_2$CO), 7.25 (5H, m, phenyl C—H), and 7.6 (4H, AB quartet, aromatic C—H).

EXAMPLE 55

Preparation of
Benzyl-5-bromo-2-(4-chlorophenyl)thiazol-4-yl-acetic ester. (Compound No. 99 in Table I)

The reaction as described in Example 52 was carried out using benzylalcohol (2 equiv., 0.65 g, 6.0 mmol) in place of neopentanol to give the desired product (0.25 g).

$^1$H NMR (CDCl$_3$) 4.05 (2H, s, CH$_2$CO), 5.25 (2H, s, OC$\underline{H}_2$C$_6$H$_5$), 7.5 (5H, m, OCH$_2$C$_6$$\underline{H}_5$), and 7.5 (4H, AB quartet, aromatic C—H).

EXAMPLE 56

Preparation of
Cyclohexylmethyl-5-bromo-2-(4-chlorophenyl)thiazol-4-yl-acetic ester. (Compound No. 100 in Table I)

The reaction as described in Example 52 was carried out using cyclohexylmethanol (2 equiv., 0.68 g, 8.0 mmol) in place of neopentanol to give the desired product (1.2 g).

$^1$H NMR (CDCl$_3$) 1.3 (11H, m, aliphatic C—H), 3.85 (2H, s, C$\underline{H}_2$CO), 3.96 (2H, d, OC$\underline{H}_2$), and 7.6 (4H, AB quartet, aromatic C—H).

EXAMPLE 57

Preparation of
p-Methoxyphenyl-5-bromo-2-(4-chlorophenyl)thiazol-4-yl acetic ester. (Compound No 101 in Table I)

The reaction as described in Example 52 was carried out using p-methoxyphenyl (2 equiv., 0.75 g, 6.0 mmol) in place of neopentanol to give the desired product (0.08 g).

$^1$H NMR (CDCl$_3$) 3.8 (3H, s, OC$\underline{H}_3$), 4.1 (2H, s, CH$_2$CO), 6.95 (4H, AB quartet, O—C$_6$$\underline{H}_4$—OMe), and 7.6 (4H, AB quartet, aromatic C—H).

EXAMPLE 58

Preparation of
n-Octyl-5-bromo-2-(4-chlorophenyl)thiazol-4-yl-acetic ester. (Compound No. 102 in Table I)

The reaction as described in Example 52 was carried out using n-octanol (2 equiv., 0.78 g, 6.0 mmol) in place of neopentanol to give the desired product (1.2 g).

$^1$H NMR (CDCl$_3$) 0.9 (3H, t, CH$_2$C$\underline{H}_3$), 1.3–1.9 (12H, m, aliphatic C—H), 3.85 (2H, s, C$\underline{H}_2$CO), 4.15 (2H, t, OC$\underline{H}_2$CH$_2$), and 7.6 (4H, AB quartet, aromatic C—H).

EXAMPLE 59

Preparation of
t-Butyl-5-chloro-2-(4-chlorophenyl)thiazol-4-yl-acetic ester. (Compound No. 103 in Table I)

The reaction as described in Example 29 was carried out using 4-butanol (2 equiv., 0.5 g, 6.9 mmol) in place of 3-methylbutanol to give the desired product (0.08 g).

$^1$H NMR (CDCl$_3$) 1.6 (9H, s, C(C$\underline{H}_3$)$_3$), 3.9 (2H, s, CH$_2$CO), and 7.75 (4H, AB quartet aromatic C—H).

EXAMPLE 60

Preparation of
(3-Chloro-2,2-dimethyl)-1-propyl-5-chloro-2-(4-chlorophenyl) thiazol-4-yl acetic ester. (Compound No. 104 in Table I)

The reaction as described in Example 29 was carried out using 3-chloro-2,2-dimethyl-1-propanol (1.1 equiv., 0.46 g, 3.7 mmol) in place of 3-methylbutanol to give the desired product.

$^1$H NMR (CDCl$_3$) 0.95 (6H, s, (C$\underline{H}_3$)$_2$), 3.35 (2H, s, CH$_2$Cl), 3.95 (2H, s, C$\underline{H}_2$CO), 4.0 (2H, s, OC$\underline{H}_2$), and 7.6 (4H, AB quartet, aromatic C—H).

EXAMPLE 61

Preparation of (Trimethylsilyl)methyl-5-chloro-2-(4-chlorophenyl)-thiazol-4-yl acetic ester. (Compound No. 105 in Table I)

The reaction as described in Example 29 was carried out using trimethylsilylmethanol (1.1 equiv) in place of 3-methylbutanol to give the desired product.

$^1$H NMR (CDCl$_3$) 0.0 (9H, s, Si(CH$_3$)$_3$), 3.8 (4H, s, CH$_2$CO and OCH$_2$Si(CH$_3$)$_3$), and 7.55 (4H, AB quartet aromatic C—H).

EXAMPLE 62

Preparation of (2-Chloromethyl)isopropyl-5-chloro2-(4-chlorophenyl)thiazol-4-yl acetic ester. (Compound No. 106 in Table I)

The reaction as described in Example 29 was carried out using 2-chloromethylisopropanol (2 equiv., 0.754 g, 6.9 mmol) and refluxing for 7 hours in place of 3-methylbutanol and stirring at room temperature for 2 hours to give the desired product (0.22 g).

$^1$H NMR (CDCl$_3$) 1.5 (6H, s, (CH$_3$)$_2$), 3.75 (2H, s, CH$_2$Cl), 3.8 (2H, s, CH$_2$CO), and 7.6 (4H, AB quartet, aromatic C—H).

EXAMPLE 63

Preparation of [2-(Methoxyethoxy)]ethyl-5-chloro-2-(4-chlorophenyl)-thiazol-4-yl acetic ester. (Compound No. 107 in Table I)

The reaction as described in Example 29 was carried out using 2-(2-methoxyethoxy)ethanol (2equiv., 0.83 g 6.9 mmol) and refluxing for 4 hours in place of 3-methylbutanol and stirring for 2 hours at room temperature to give the desired product (0.33 g).

$^1$H NMR (CDCl$_3$) 3.3 (3H, s, OCH$_3$), 3.5 (2H, m, OCH$_2$CH$_2$OCH$_3$), 3.6 (2H, m, OCH$_2$CH$_2$OCH$_3$), 3.7 (2H, t, OCH$_2$CH$_2$), 3.9 (2H, s, CH$_2$CO), 4.3 (2H, t, OCH$_2$CH$_2$), and 7.6 (4H, AB quartet aromatic C—H).

EXAMPLE 64

Preparation of Ethylglycolyl-5-chloro-2-(4-chlorophenyl)thiazol-4-yl acetic ester (Compound No. 108 in Table I)

The reaction as described in Example 29 was carried out using ethylglycolate (2 equiv., 0.723 g, 6.9 mmol) and refluxing for 10 hours in place of 3-methylbutanol and stirring for 2 hours at room temperature to give the desired product (0.4 g).

$^1$H NMR (CDCl$_3$) 1.2 (3H, t, OCH$_2$CH$_3$), 4.0 (2H, s, CH$_2$CO), 4.2 (2H, q, OCH$_2$CH$_3$), 4.7 (2H, s, OCH$_2$CO$_2$Et), and 7.6 (4H, AB quartet, aromatic C—H).

EXAMPLE 65

Preparation of Tetrahydrofurfuryl-5-chloro-2-(4-chlorophenyl)-thiazol-4-yl acetic ester. (Compound No. 109 in Table I)

The reaction as described in Example 29 was carried out using tetrahydrofurfuryl alcohol (2 equiv., 8.7 g, 6.9 mmol) in place of 3-methylbutanol to give the desired product (0.35 g).

$^1$H NMR (CDCl$_3$) 1.95 (4H, m, aliphatic C—H), 3.9 9(2H, m, —O—CH$_2$), 4.0 (2H, s, CH$_2$CO), 4.25 (3H, m, O—CH$_2$—CH—O), and 7.7 (4H, AB quartet, aromatic C—H).

EXAMPLE 66

Preparation of Ethylmandelyl-5-chloro-2-(4-chlorophenyl)thiazol-4-yl acetic ester. (Compound No. 110 in Table I)

The reaction as described in Example 64 was carried out using ethylmandelate (2 equiv., 1.25 g, 6.9 mmol) in place of ethylglycolate to give the desired product.

$^1$H NMR (CDCl$_3$) 1.2 (3H, t, OCH$_2$CH$_3$), 4.0 (2H, s, CH$_2$CO), 4.25 (2H, m, OCH$_2$CH$_3$), 6.0 (1H, s, OCHC$_6$H$_5$), 7.35 (3H, m, phenyl -H), 7.50 (2H, m, phenyl-H), and 7.55 (4H, ABq, aromatic C—H).

EXAMPLE 67

Preparation of (α)-γ-Butyrolactonyl-5-bromo-2-(4-chlorophenyl)-thiazol-4-yl acetic ester. (Compound No. 111 In Table I)

The reaction as described in Example 52 was carried out using α-hydroxy-γ-butyrolactone (2 equiv, 0.61 g, 6.0 mmol) and stirring at room temperature for 2 days in place of neopentanol and stirring at room temperature for 2 hours to give the desired product (0.13 g).

$^1$H NMR (CDCl$_3$) 2.3 (1H, m,

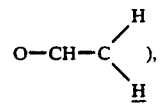

), 2.75 (1H, m,

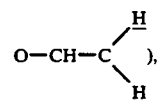

), 3.95 (2H, s, CH$_2$CO), 4.3 (1H, m,

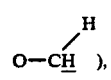

), 4.45 (1H, m,

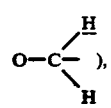

), 5.5 (1H, t, O—CH) and 7.6 (4H, AB quartet, aromatic (C—H).

EXAMPLE 68

Preparation of Methyllactatyl-5-bromo-2-(4-chlorophenyl)thiazol-4-yl acetic ester. (Compound No. 112 in Table I)

The reaction as described in Example 64 was carried out using 5-bromo-2-(4-chlorophenyl)thiazol-4-yl acetic acid and methyllactate (2 equiv., 0.723 g, 6.9 mmol) in place of 5-chloro-2-(4-chlorophenyl)thiazol-4-yl acetic acid and ether glycolate to give the desired product (0.4 g).

$^1$H NMR (CDCl$_3$) 1.5 (3H, d, CH(CH$_3$), 3.75 (3H, s, OCH$_3$), 3.95 (2H, s, CH$_2$CO), 5.2 (1H, q, CH(CH$_3$), and 7.6 (4H, AB quartet, aromatic C—H).

EXAMPLE 69

Preparation of
Ethylmandelyl-5-bromo-2-(4-chlorophenyl)thiazol-4-yl acetic ester. (Compound No. 113 in Table I)

The reaction as described in Example 67 was carried out using ethylmandelate (2 equiv., 1.08 g, 6.0 mmol) in the place of α-hydroxy-γ-butyrolactone to give the desired product (0.36 g).

$^1$H NMR (CDCl$_3$) 1.2 (3H, t, OCH$_2$CH$_3$), 4.0 (2H, s, CH$_2$CO), 4.2 (2H, m, OCH$_2$CH$_3$), 6.0 (1H, s, O—CH), 7.35 (3H, m, phenyl-H), 7.50 (2H, m, phenyl-H), and 7.55 (4H, AB quartet, aromatic C—H).

EXAMPLE 70

Preparation of
Ethylglycolyl-5-bromo-2-(4-chlorophenyl)thiazol-4-yl acetic ester. (Compound No. 114 in Table I)

The reaction as described in EXAMPLE 67 was carried out using ethylglycolate (2 equiv, 8.626 g, 6.0 mmol) in place of α-hydroxy-β-butyolactone to give the desired product (0.2 g).

$^1$H NMR (CDCl$_3$) 1.25 (3H, t, OCH$_2$CH$_3$), 4.0 (2H, s, CH$_2$CO), 4.2 (2H, q, OCH$_2$CH$_3$), 4.7 (2H s, OCH$_2$CO$_2$Et), and 7.6 (4H, AB quartet, aromatic C—H).

EXAMPLE 71

Preparation of
(2-Methoxyethoxy)ethyl-5-bromo-2-(4-chlorophenyl)-thiazol-4-yl acetic acid. (Compound No. 115 in Table I)

The reaction as described in Example 67 was carried out using 2-methoxyethoxyethanol (2 equiv., 0.72 g, 6.0 mmol) in place of α-hydroxy-β-butylolactone to give the desired product (0.46 g).

$^1$H NMR (3.35 (3H, s, OCH$_3$), 3.55 (4H, m, OCH$_2$CH$_2$OCH$_3$), 3.7 (2H, t, OCH$_2$CH$_2$O), 3.9 (2H, s, CH$_2$CO), 4.3 (2H, t, OCH$_2$CH$_2$O), and 7.6 (4H, AB quartet, aromatic C—H).

EXAMPLE 72

Preparation of
Methylmandelyl-5-bromo-2-(4-chlorophenyl)thiazol-4-yl acid ester. (Compound No. 116 in Table I)

The reaction as described in Example 67 was carried out using methylmandelate (2 equiv, 0.725 g, 6.0 mmol) in place of α-hydroxy-β-butyolactone to give the desired product (0.46 g).

$^1$H NMR (CDCl$_3$) 3.7 (3H, s, OCH$_3$), 4.0 (2H, s, CH$_2$CO), 6.0 (1H, s, OCH), 7.35 (3H, m, phenyl C—H), 7.5 (2H, m, phenyl C—H), and 7.55 (4H, AB quartet, aromatic C—H).

EXAMPLE 73

Preparation of
Methylmandelyl-5-chloro-2-(4-chlorophenyl)thiazol-4-yl acetic ester. (Compound No. 117 in Table I)

The reaction as described in Example 64 was carried out using methylmandelate (2 equiv, 1.15 g 6.9 mmol) in place of ethyl glycollate to give the desired product (0.32 g).

$^1$H NMR (CDCl$_3$) 3.75 (3H, s, OCH$_3$), 4.0 (2H, s, CH$_2$CO), 6.0 (1H, s, OCH), 7.35 (3H, m, phenyl C—H), 7.5 (2H, m, phenyl C—H and 7.55 (4H, AB quartet, aromatic C—H).

EXAMPLE 74

Preparation of
(3,3,2,2-Tetrafluoro-2-methyl-2-butyl)-5-chloro-2-(4-chlorophenyl)thiazol-4-yl acetic ester. (Compound No. 118 in Table I)

The reaction as described in Example 64 was carried out using 3,3,2,2-tetrafluoro-2-methyl-2-butanol (2 equiv, 1.11 g, 6.9 mmol) in place of ethylglycolate to give the desired product (0.5 g).

$^1$H NMR (CDCl$_3$) 1.28 (3H, s, CH$_3$), 1.32 (3H, s, CH$_3$), 3.8 (2H, s, CH$_2$CO), 5.9 (1H, m, CHF$_2$), and 7.6 (4H, AB quartet, aromatic C—H).

EXAMPLE 75

Preparation of Methyl
S(—)-lactatyl-5-chloro-2-(4-chlorophenyl)thiazol-4-yl acetic ester. (Compound No. 119 in Table I)

The reaction as described in Example 64 was carried out using methyl-S(—)-lactate (2 equiv, 1.15 g, 6.9 mmol) in place of ethylglycolate to give the desired product (0.4 g).

$^1$H NMR (CDCl$_3$) 1.5 (3H, d, CH(CH$_3$), 3.7 (3H, s, OCH$_3$), 3.9 (2H, s, CH$_2$CO), 5.2 (1H, q, CH(CH$_3$), and 7.6 (4H, AB quartet, aromatic C—H).

EXAMPLE 76

Preparation of
Ethylglycinyl-5-chloro-2-(4-chlorophenyl)thiazol-4-yl acetic ester. (Compound No. 120 in Table I)

The reaction as described in Example 29 was carried out using ethylglycine (2 equiv., 0.9 g) and stirring at room temperature for 2 days in place of 3-methyl butanol and stirring at room temperature for 2 hours to give the desired product (0.06 g).

$^1$H NMR (CDCl$_3$) 1.2 (3H, t, OCH$_2$CH$_3$), 3.8 (2H, s, CH$_2$CO), 4.1 (2H, s, CH$_2$CO), 4.2 (2H, quartet, OCH$_2$CH$_3$O), 7.5 (1H, bs, HNCH$_2$CO$_2$Et), and 7.7 (4H, AB quartet, aromatic C—H).

EXAMPLE 77

Preparation of
(4)-butyrolactonyl-5-chloro-2-(4-chlorophenyl)thiazol-4-yl acetic ester. (Compound No. 121 in Table I)

The reaction as described in Example 29 was carried out using α-hydroxy-γ-butyrolactone (2 equiv., 0.7 g, 6.9 mmol) in place of 3-methylbutanol to give the desired product (0.38 g).

$^1$H NMR (CDCl$_3$) 2.35 (1H, m,

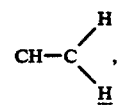

2.75 (1H, m,

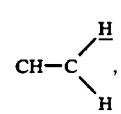

3.95 (2H, s, CH$_2$CO), 4.4 (2H, m, O—CH$_2$), 5.5 (1H, t, OCH), and 7.6 (4H, AB quartet, aromatic C—H).

EXAMPLE 78

Preparation of
Ethyl-5-chloro-2-(4-chlorophenyl)thiazol-4-yl
bromoacetic ester. (Compound No. 122 in Table I)

Lithium hexamethyldisilazane (LHMDS) (1 equiv., 1M solution in THF, 6.32 ml, 6.3 mmol) was added dropwise to ethyl-5-chloro-2-(4-chlorophenyl)thiazol-4-yl acetic ester dissolved in dry THF (50 ml) at $-70°$ C. under $N_2$. The reaction mixture was allowed to stir for 10 minutes followed by the addition of NBS (1 equiv., 1.12 g, 6.3 mmol) in THF (10 ml) and then allowed to warm to room temperature. The precipitate was removed by suction and the filtrate was concentrated under reduced pressure and the product was purified by flash chromatography (eluted with 10% $Et_2O$/Hexane) (1.7 g).

$^1$H NMR (CDCl$_3$) 1.3 (3H, t, OCH$_2$CH$_3$), 4.2 (2H, q, OCH$_2$CH$_3$), 5.7 (1H, s, CHBr) and 7.6 (4H, AB quartet, aromatic C—H).

EXAMPLE 79

Preparation of Compound No. 123 in Table I

LHMDS (1 equiv., 0.26 g, 1.57 mmol) was added dropwise to ethyl-5-chloro-2-(4-chlorophenyl)thiazol-4-yl acetic the resulting mixture stirred for 15 minutes. Benzylchloroformate (1 equiv., 0.27 g, 0.23, 1.57 mmol) was added and the reaction mixture was allowed to warm to room temperature and stirred for 48 hours. Sat NH$_4$Cl solution was added and the organic layer separated, and concentrated under reduced pressure. The product (0.25 g) was purified by chromatography (eluted with 10% E$_2$O/Hexane).

$^1$H NMR (CDCl$_3$) 1.05 (3H, t, OCH$_2$CH$_3$), 4.05 (2H, quartet, OCH$_2$CH$_3$), 4.8 (1H, s, CHCO$_2$CH$_2$C$_6$H$_5$), 5.05 (2H, s, OCH$_2$C$_6$H$_5$), 7.1 (5H, m, phenyl C—H), and 7.3 (4H, AB quartet, aromatic C—H).

EXAMPLE 80

Preparation of
Ethyl-5-chloro-2-(4-chlorophenyl)thiazol-4-yl
chloroacetic ester. (Compound No. 124 in Table I)

The reaction as described in Example 78 was carried out using NCS (1 equiv., 0.21 g, 1.57 mmol), in place of NBS to give the desired product (0.3 g).

$^1$H NMR (CDCl$_3$) 1.3 (3H, t, OCH$_2$CH$_3$), 4.3 (2H, q, OCH$_2$CH$_3$), 5.7 (1H, s, CH$_{Cl}$, and 7.6 (4H, AB quartet, aromatic C—H).

EXAMPLE 81

Preparation of Compound No. 125 in Table I)

A mixture of Cu(I)CN (1 equiv., 0.115 g, 1.57 mmol), N-methylpyrolidinone (5 ml) and the thiazole derivative (compound No. 61) (500 mg, 1.57 mmol) were heated at 140° C. for 10 minutes. The reaction mixture was cooled and the solvent distilled off (approx 44° under high vac.) and the residue partitioned between CHCl$_3$ and H$_2$O. The insoluble salts were filtered off under suction, the organic layer separated, dried (MgSO$_4$), filtered and concentrated under reduced pressure. The product (0.1 g) was purified by chromatography (eluted with 10% Et$_2$O/Hexane).

$^1$H NMR (CDCl$_3$) 1.45 (3H, t, OCH$_2$CH$_3$), 4.5 (2H, q, OCH$_2$CH$_3$) and 7.65 (4H, AB quartet, aromatic C—H).

EXAMPLE 82

Preparation of
Methyl-5-nitro-2-(4-chlorophenyl)thiazol-4-yl acetic
ester. (Compound No. 126 in Table I)

Methyl-2-(4-chlorophenyl)thiazol-4-yl acetic ester (5.0 g, 18.7 mmol) in CH$_3$CN (dry, 10 ml) was carefully added dropwise to BF$_4$NO$_2$ (0.5 equiv., 1.25 g, 9.3 mmol) suspended in CH$_3$CN (50 ml) at 5° C. (ice/salt bath). When all the BF$_4$NO$_2$ salt had dissolved, H$_2$O (10 ml) was added, and the mixture concentrated under reduced pressure to approximately 20 ml volume. The solution was extracted with CHCl$_3$ and the combined organic extracts dried (MgSO$_4$), filtered and concentrated under reduced pressure. The product (1.5 g) was purified by chromatography (eluted with 25% Et$_2$O/Hexane).

$^1$H NMR (CDCl$_3$) 3.8 (3H, s, OCH$_3$), 4.3 (2H, s, CH$_2$CO) and 7.7 (4H, AB quartet, aromatic C—H).

EXAMPLE 83

Preparation of
Methyl-5-bromo-2-(4-fluorophenyl)thiazol-4-yl acetic
ester. (Compound No. 127 in Table I)

Bromine (1.6 g, 0.52 ml, 10 mmol) was added dropwise to 2-(4-fluorophenyl)thiazol-4-yl acetic acid (2.37 g, 10 mmol) dissolved in AcOH (30 ml) and the resulting mixture stirred at room temperature for 2 hours. The precipitate was separated by suction, washed with CH$_2$C$_2$ and air dried to yield the corresponding 5-bromo thiazole acid derivative. This was esterified in the usual way to give the desired product (2.0 g).

$^1$H NMR (CDCl$_3$) 3.75 (3H, s, OCH$_3$), 3.9 (2H, s, CH$_2$CO), 7.1 (2H, t, aromatic C—H), and 7.85 (2H, dd, aromatic C—H).

EXAMPLE 84

Preparation of
Ethyl-5-bromo-2-(4-fluorophenyl)thiazol-4-yl acetic
ester. (Compound No. 128 in Table I)

5-bromo-2-(4-fluorophenyl)thiazol-4-yl acetic acid (0.5 g, 1.58 mmol) (preparation outlined in Example 83) was esterified in the usual way (see Example 3) to give the desired product (0.46 g).

$^1$H NMR (CDCl$_3$) 1.28 (3H, t, OCH$_2$CH$_3$), 3.85 (2H, s, CH$_2$CO), 4.25 (2H, q, OCH$_2$CH$_3$), 7.12 (2H, m, aromatic C—H), and 7.8 (2H, m, aromatic C—H).

EXAMPLE 85

Preparation of
n-Pentyl-5-bromo-2-(4-chlorophenyl)thiazol-4-yl acetic
ester. (Compound No. 129 in Table I)

The reaction as described in Example 52 was carried out using n-pentanol (2 equiv, 0.53 g, 6 mmol) in place of neopentanol to give the desired product (0.4 g).

$^1$H NMR (CDCl$_3$) 0.85 (3H, t, CH$_2$CH$_3$), 1.3 (4H, m, aliphatic H's), 1.63 (2H, m, aliphatic H), 3.85 (2H, s, CH$_2$CO), 4.15 (2H, t, OCH$_2$CH$_2$), and 7.6 (4H, AB quartet, aromatic C—H).

EXAMPLE 86

Preparation of
n-Hexyl-5-bromo-2-(4-chlorophenyl)thiazol-4-yl acetic
ester. (Compound No. 130 in Table I)

The reaction as described in Example 52 was carried out using n-hexanol (2 equiv, 0.614 g, 6.0 mmol), in place of neopentanol to give the desired product (0.35 g).

$^1$H NMR (CDCl$_3$) 1.0 (3H, t, CH$_2$CH$_3$), 1.45 (8H, m, aliphatic H), 1.8 (2H, m, aliphatic H), 4.0 (2H, s, CH$_2$CO), 4.3 (2H, t, OCH$_2$CH$_2$), and 7.75 (4H AB quartet, aromatic C—H).

EXAMPLE 87

Preparation of Ethyl-5-chloro-2-(4-chlorophenyl)thiazol-4-yl fluoroacetic ester. (Compound No. 132 in Table I)

A mixture of ethyl-5-chloro-2-(4-chlorophenyl)-thiazol-4-yl bromoacetic ester (Compound No. 122) (1 g, 2.5 mmol), CsF (3 equiv., 1.15 g, 7.5 mmol) and dry DMF (10 ml) were heated at 130° C. for 1 hour. The reaction mixture was cooled and then concentrated under reduced pressure. The product (0.15 g) was purified by chromatography (eluted with 20% Et$_2$O/Hexane).

$^1$H NMR (CDCl$_3$) 1.35 (3H, t, OCH$_2$CH$_3$), 4.35 (2H, q, OCH$_2$CH$_3$), 6.05 (1H, d, CHF) and 7.6 (4H, AB quartet, aromatic C—H).

EXAMPLE 88

Preparation of Methyl-5-nitro-2-(4-fluorophenyl)thiazol-4-yl acetic ester. (Compound No. 137 in Table I)

The reaction as described in Example 82 was carried out using methyl-2-(4-fluorophenyl)thiazol-4-yl acetic ester (Compound No. 139) (1.5 g, 5.6 mmol) in place of methyl-2-(4-chlorophenyl)thiazol-4-yl acetic ester to give the desired product (0.2 g).

$^1$H NMR (CDCl$_3$) 3.75 (3H, s, OCH$_3$), 4.3 (2H, s, CHCO), 7.2 (2H, dd, aromatic C—H), and 8.0 (2H, dd, aromatic C—H).

EXAMPLE 89

Preparation of 5-Bromo-2-(3-chlorophenyl)thiazol-4-yl acetic acid. (Compound No. 140 in Table I)

The reaction as described in Example I was carried out using 2-(3-chlorophenyl)thiazol-4-yl acetic acid in place of 2-)4-chlorophenyl)thiazol-4-yl acetic acid to give the desired product.

$^1$H NMR (d$_6$-DMSO) 3.92 (2H, s, CH$_2$CO), 7.4 (2H, m, aromatic C—H), 7.70 (1H, m, aromatic C—H), and 7.87 (1H, d, aromatic C—H).

EXAMPLE 90

Preparation of Ethyl-5-bromo-2-phenylthiazol-4-yl acetic ester. (Compound No. 141 in Table I)

5-bromo-2-phenylthiazol-4-yl acetic acid, (obtained by simple bromination on the corresponding acid, see for e.g., Example 83) (0.5 g, 1.68 mmol) was esterified in the usual way to give the desired product (0.13 g).

$^1$H NMR (CDCl$_3$) 1.3 (3H, t, OCH$_2$CH$_3$), 3.85 (2H, s, CH$_2$CO), 4.2 (2H, q, OCH$_2$CH$_3$), 7.4 (3H, m, aromatic C—H), and 7.85 (2H, m, aromatic C—H).

EXAMPLE 91

Preparation of Methyl-5-bromo-2-phenylthiazol-4-yl acetic ester. (Compound No. 142 in Table I)

The reaction as described in Example 3 was carried out using 5-bromo-2-phenylthiazol-4l-yl acetic acid (0.5 g, 1.68 mmol) in place of 5-bromo-2-(4-chlorophenyl)-thiazol-4-yl acetic acid to give the desired product (0.17 g).

$^1$H NMR (CDCl$_3$) 3.75 (3H, s, OCH$_3$), 3.9 (2H, s, CH$_2$CO), 7.4 (3H, m, aromatic C—H), and 7.85 (2H, m, aromatic C—H).

EXAMPLE 92

Preparation of Ethyl-5-bromo-2-(3-chlorophenyl)thiazol-4-yl acetic ester. (Compound No. 143 in Table I)

5-bromo-2-(3-chlorophenyl)thiazol-4-yl acetic acid (0.4 g, 1.2 mmol) was esterified in the usual way to give the desired product (0.25 g).

$^1$H NMR (CDCl$_3$) 1.3 (3H, t, OCH$_2$CH$_3$), 3.85 (2H, s, CH$_2$CO), 4.2 (2H, q, OCH$_2$CH$_3$), 7.4 (2H, m, aromatic C—H), 7.7 (1H, m, aromatic C—H), and 7.9 (1H, m, aromatic C—H).

EXAMPLE 93

Preparation of Methyl-5-bromo-2-(3-chlorophenyl)thiazol-4-yl acetic ester. (Compound No. 144 in Table I)

The compound was prepared by methods analogous to that described in Example 92.

$^1$H NMR (CDCl$_3$) 3.75 (3H, s, OCH$_3$), 3.9 (2H, s, CH$_2$CO), 7.4 (2H, m, aromatic C—H), 7.7 (1H, m, aromatic C—H), and 7.9 (1H, d, aromatic C—H).

EXAMPLE 94

Preparation of Methyl-5-bromo-2-(4-chlorophenyl)thiazol-4-yl bromoacetic ester. (Compound No. 145 in Table I)

A mixture of 2-(4-chlorophenyl)thiazol-4-ylacetic acid (8.0 g, 31.6 mmol), bromine (2 ml) and acetic acid (100 ml) were heated at 100° C. for 1.5 hours. The reaction mixture was cooled, and the precipitate separated by suction. Half of the solid was refluxed in methanol for 5 hours. The reaction mixture was concentrated and the product (1.1 g) purified by chromatography.

$^1$H NMR (CDCl$_3$) 3.85 (3H, s, OCH$_3$), 5.75 (1H, s, CHBr), and 7.65 (4H, AB quartet, aromatic C—H).

EXAMPLE 95

Preparation of Ethyl-5-bromo-(4-chlorophenyl)thiazol-4-yl bromoacetic ester. (Compound No. 146 in Table I)

The remaining half of the solid from Example 94 was refluxed in ethanol for 5 hours. The reaction mixture was cooled, filtered and the filtrated concentrated under reduced pressure. The product (1.0 g) was purified by chromatography.

$^1$H NMR (CDCl$_3$) 1.3 (3H, t, OCH$_2$CH$_3$), 4.2 (2H, q, OCH$_2$CH$_3$), 5.7 (1H, s, CHBr), and 7.65 (4H, AB quartet, aromatic C—H).

EXAMPLE 96

Preparation of methyl-5-bromo-2-(4-bromophenyl)thiazol-4-yl acetic ester. (Compound No. 147 in Table I)

This compound was prepared by methods analogous to those described in Example 2.

$^1$H NMR (CDCl$_3$) 3.75 (3H, s, OCH$_3$), 3.9 (2H, s, CH$_2$CO), and 7.65 (4H, AB quartet, aromatic C—H).

EXAMPLE 97

Preparation of
Ethyl-5-bromo-2-(4-bromophenyl)thiazol-4-yl acetic ester. (Compound No. 148 in Table I)

This compound was prepared by methods analogous to those described in Example 3.

$^1$H NMR (CDCl$_3$) 1.3 (3H, t, OCH$_2$CH$_3$), 3.85 (CH$_2$CO), 4.2 (2H, q, OCH$_2$CH$_3$), and 7.65 (4H, AB quartet, aromatic C—H).

EXAMPLE 98

Preparation of
n-Propyl-5-bromo-2-(4-bromophenyl)thiazol-4-yl acetic ester. (Compound No. 149 in Table I)

This compound was prepared by methods analogous to those described in Example 7.

$^1$H NMR (CDCl$_3$) 0.95 (3H, s, OCH$_2$CH$_2$CH$_3$), 1.7 (2H, sextet, OCH$_2$CH$_2$CH$_3$), 3.85 (2H, s, CH$_2$CO), 4.1 (2H, t, OCH$_2$CH$_2$CH$_3$), and 7.65 (4H, AB quartet, aromatic C—H).

EXAMPLE 99

Preparation of 5-Bromo-2-(4-bromophenyl)thiazol-4-yl acetic acid. (Compound No. 150 in Table I)

The reaction as described in Example 83 was carried out using 2-(4-bromophenyl)thiazol-4-yl acetic acid (4 g, 13.5 mmol) to give the desired product (3.76 g).

$^1$H NMR (D$_6$-DMSO+CDCl$_3$) 3.75 (2H, s, CH$_2$CO), 7.8 (4H, AB quartet, aromatic C—H).

EXAMPLE 100

Preparation of
5-Bromo-2-(4-trifluoromethylphenyl)thiazol-4-yl acetic acid. (Compound No. 151 in Table I)

This compound was prepared by methods analogous to those described in Example 83.

$^1$H NMR (D$_6$-DMSO+CDCl$_3$) 3.9 (2H, s, CH$_2$CO$_2$H), and 7.85 (4H, AB quartet, aromatic C—H).

EXAMPLE 101

Preparation of
Methyl-5-bromo-2-(4-trifluoromethylphenyl)thiazol-4-yl acetic ester. (Compound No. 152 in Table I)

This compound was prepared by a reaction analogous to that described in Example 83 followed by esterification as described in Example 2.

$^1$H NMR (CDCl$_3$) 3.75 (3H, s, CO$_2$CH$_3$), 3.9 (2H, s, CH$_2$CO), and 7.8 (4H, AB quartet, aromatic C—H).

EXAMPLE 102

Preparation of
Ethyl-5-bromo-2-(4-trifluoromethylphenyl)thiazol-4-yl acetic ester. (Compound No. 153 in Table I)

This compound was prepared by methods analogous to those described in Example 83 followed by esterification as described in Example 3.

$^1$H NMR (CDCl$_3$) 1.3 (3H, t, OCH$_2$CH$_3$), 3.9 (2H, s, CH$_2$CO), 4.2 (2H, q, OCH$_2$CH$_3$), and 7.8 (4H, AB quartet, aromatic C—H).

EXAMPLE 103

Preparation of
Methyl-5-amino-2-(4-chlorophenyl)thiazol-4-yl acetic ester. (Compound No. 154 in Table I)

Methyl-5-nitro-2-(4-chlorophenyl)thiazol-4-yl acetic ester (Compound No. 126) (0.85 g) in MeOH/CHCl$_3$ (50 ml, 5 ml) was hydrogenated over 10% palladium on charcoal (cat). The product (0.2 g) was purified by chromatography (eluted with 20% Et$_2$O/Hexane).

$^1$H NMR (CDCl$_3$) 3.7 (3H, s, CO$_2$CH$_3$), 3.8 (2H, s, CH$_2$CO), and 7.5 (4H, AB quartet, aromatic C—H).

EXAMPLE 104

Preparation of
5-Bromo-2-(2,4-difluorophenyl)thiazol-4-yl acetic acid. (Compound No. 155 in Table I)

This compound was prepared by methods analogous to those described in Example 83.

$^1$H NMR (CDCl$_3$) 3.75 (2H, s, CH$_2$CO), 7.53 (1H, m, aromatic C—H), 7.74 (7H, m, aromatic C—H), 7.9 (1H, m, aromatic C—H) and 12.5 (1H, bs, CO$_2$H).

EXAMPLE 105

Preparation of
Methyl-5-bromo-2-(2,4-difluorophenyl)thiazol-4-yl acetic ester. (Compound No. 157 in Table I)

This compound was prepared by methods analogous to that described in Example 83 followed by esterification as described in Example 2.

$^1$H NMR (CDCl$_3$) 3.8 (3H, s, CO$_2$CH$_3$), 4.1 (2H, s, CH$_2$CO), 7.0 (1H, m, aromatic C—H), 7.1 (1H, m, aromatic C—H), and 8.65 (1H, m, aromatic C—H).

EXAMPLE 106

Preparation of
Ethyl-5-bromo-2-(2,4-difluorophenyl)thiazol-4-yl acetic ester. (Compound No. 158 in Table I)

This compound was prepared by a method as described in Example 83 followed by esterification as described in Example 3.

$^1$H NMR (CDCl$_3$) 1.3 (3H, t, OCH$_2$CH$_3$), 4.15 (2H, s, CH$_2$CO), 4.25 (2H, q, OCH$_2$CH$_3$), 7.0 (1H, m, aromatic C—H), 7.12 (1H, m, aromatic C—H), and 8.7 (1H, m, aromatic C—H).

EXAMPLE 107

Preparation of
Methyl-5-bromo-2-(3,4-difluorophenyl)thiazol-4-yl acetic ester. (Compound No. 159 in Table I)

This compound was prepared as described in Example 83 followed by esterification as described in Example 2.

$^1$H NMR (CDCl$_3$) 3.75 (3H, s, CO$_2$CH$_3$), 3.88 (2H, s, CH$_2$CO), 7.25 (1H, m, aromatic C—H), 7.6 aromatic C—H).

EXAMPLE 108

Preparation of
Ethyl-5-bromo-2-(3,4-difluorophenyl)thiazol-4-yl acetic ester. (Compound No 160 in Table I)

This compound was prepared as described in Example 83 followed by esterification as described in Example 3.

¹H NMR (CDCl₃+d₆DMSO) 1.33 (3H, t, OCH₂C$\underline{H}$₃), 4.28 (2H, q, OC$\underline{H}$₂CH₃), 4.32 (2H, s, C$\underline{H}$₂CO), 7.4 (1H, m, aromatic C—H), and 8.15 (2H, m, aromatic C—H).

EXAMPLE 109

Preparation of 5-Bromo-2-phenylthiazol-4-yl acetic acid. (Compound No. 162 in Table I)

This compound was prepared by a method as described in Example 83.

¹H NMR (CDCl₃+d₆DMSO) 3.85 (2H, s, C$\underline{H}$₂CO), 7.45 (3H, m, aromatic C—H), and 7.89 (2H, m, aromatic C—H).

EXAMPLE 110

Preparation of 5-Bromo-2-(4-flurophenyl)thiazol-4-yl acetic acid. (Compound No. 163 in Table I)

This compound was prepared by methods analogous to that described in Example 83.

¹H NMR (CDCl₃+d₆DMSO) 3.84 (2H, s, C$\underline{H}$₂CO), 7.13 (1H, t, aromatic C—H), 7.8 (1H, m, aromatic C—H), and 8.05 (1H, m, aromatic C—H).

EXAMPLE 111

Preparation of N,N-Dimethyl-5-bromo-2-(2,6-difluorophenyl)thiazol-4-yl acetamide. (Compound No. 164 in Table I)

The reaction as described in Example 83 was carried out using N,N-dimethyl-2-(2,6-difluorophenyl)thiazol-4-yl acetamide (1 g, 3.5 mmol) to give the desired product (1.1 g).

¹H NMR (d₆DMSO) 2.95 (3H, s, NC$\underline{H}$₃), 3.2 (3H, s, NC$\underline{H}$₃), 4.0 (2H, s, C$\underline{H}$₂CO), 7.4 (2H, m, aromatic C—H), and 7.7 (1H, m, aromatic C—H).

EXAMPLE 112

Preparation of N,N-Dimethyl-5-bromo-2-(4-chlorophenyl)thiazol-4-yl acetohydrazide. (Compound No. 165 in Table I)

The reaction as described in Example 52 was carried out using N,N-dimethylhydrazine (0.28 g, 4.84 mmol) in place of neopentanol to give the desired product (recrystallised from EtOAc) (1.08 g).

¹H NMR (CDCl₃) 2.55 (3H, s, NC$\underline{H}$₃), 2.60 (3H, s, NC$\underline{H}$₃), 4.0 (2H, s, C$\underline{H}$₂CO), 6.1 (1H, bs, $\underline{H}$NN (CH₃)₂), and 7.65 (4H, AB quartet aromatic (C—H).

EXAMPLE 113

Preparation of Compound No. 166 in Table 1

Iodomethane (2 ml excess) was added dropwise to N,N-dimethyl-5-bromo-2-(4-chlorophenyl)thiazol-4-yl acetohydrazide (Example 112), (0.52 g, 1.4 mmol) suspended in dry methanol (15 ml) and the result solution stirred at room temperature for 24 hours. The reaction mixture was concentrated under reduced pressure, and the residue triturated with Et₂O to give the desired product (0.14 g).

¹H NMR (d₆ DMSO) 3.9 (9H, s,N(C$\underline{H}$₃)₃), 3.95 (2H, s, C$\underline{H}$₂CO), and 7.6 (4H, AB quartet, aromatic C—H).

EXAMPLE 114

Preparation of Methyl-5-bromo-2-(4-toluyl)thiazol-4-yl acetic ester. (Compound No. 167 in Table I)

This compound was prepared by a method as described in Example 83 followed by esterification as described in Example 2.

¹H NMR (CDCl₃) 3.4 (3H, s, aromatic CH₃), 3.75 (3H, s, CO₂C$\underline{H}$₃), 3.90 (2H, s, CH₂CO), and 7.5 (4H, AB quartet, aromatic C—H).

EXAMPLE 115

Preparation of Ethyl-5-bromo-2-(4-chlorophenyl)thiazol-4-yl thioacetic ester. (Compound No. 168 in Table I A mixture of 5-bromo-2-(4-chlorophenyl)thiazol-4-yl acetic acid (0.5 g 1.5 mmol), EtSH (2 equiv., 0.254 g, 3.0 mmol), pyridine (3 equiv., 0.625 g) and phenyl dichlorophosphate (1.5 equiv, 0.63 g) was stirred at room temperature for 8 hours. The mixture was poured into iced water and extracted with CHCl₃. The combined organic extracts were dried (MgSO₄), filtered and concentrated under reduced pressure. The product (0.17 g) was purified by chromatography (eluted with 5% Et₂O/Hexane).

¹H NMR (CDCl₃) 1.3 (3H, t, SCH₂C$\underline{H}$₃), 2.9 (2H, q, SC$\underline{H}$₂CH₃), 4.05 (2H, s, C$\underline{H}$₂CO), and 7.65 (4H, AB quartet aromatic C—H).

EXAMPLE 116

Preparation of Methyl-5-bromo-2-(4-methoxyphenyl)thiazol-4-yl acetic ester. (Compound No. 169 in Table I).

This compound was prepared by a method as described in Example 83 followed by esterification as described in Example 2.

¹H NMR (CDCl₃) 3.75 (2H, s, C$\underline{H}$₂CO), 3.85 (6H, s, CO₂ C$\underline{H}$₃), 7.4 (4H, AB quartet, aromatic C—H).

EXAMPLE 117

Preparation of 5-Bromo-2-(4-methoxyphenyl)thiazol-4-yl acetic acid. (Compound No. 170 in Table I)

This compound was prepared by a method as described in Example 83

¹H NMR (d₆ DMSO) 3.85 (2H, s, C$\underline{H}$₂CO₂H), 3.87 (3H, s, OC$\underline{H}$₃), and 7.45 (4H, AB quartet, C—H).

EXAMPLE 118

Preparation of Methyl-5-bromo-2-(4-trifluoromethoxy phenyl) thiazol-4-yl acetic ester. (Compound No. 171 in Table I)

This compound was prepared by a method as described in Example 83 followed by esterification as described in Example 2.

¹H NMR (CDCl₃) 3.75 (3H, s, CO₂CH₃), 3.9 (2H, s, C$\underline{H}$₂CO), and 7.6 (4H, AB quartet, aromatic C—H).

EXAMPLE 119

Preparation of 5-Bromo-2-(4-acetylphenyl)thiazol-4-yl acetic acid. (Compound No. 172 in Table I)

This compound was prepared by a method as described in Example 83.

¹H NMR (d₆-DMSO) 2.6 (3H, s, COCH₃), 3.83 (2H, s, C$\underline{H}$₂CO), and 8.0 (4H, m, aromatic C—H).

EXAMPLE 120

Preparation of Methyl-2-(4-chlorophenyl)thiazol-4-yl fluoroacetic ester. (Compound No. 173 in Table I)

A mixture of methyl-5-bromo-2-(4-chlorophenyl)-thiazol-4-yl acetic ester (0.5 g, 1.4 mmol), Ag(I)F (2 equiv., 0.35 g, 2.8 mmol). and CH$_3$CN (dry, 10 ml) were stirred at room temperature for 24 hours. The reaction mixture was filtered and filtrate concentrated under reduced pressure to give the desired product (0.22 g).

$^1$H NMR (CDCl$_3$) 3.9 (3H, s, CO$_2$CH$_3$), 6.0 (1H, d, CHF), 5.5 (1H, s, thiazole ring H), and 7.7 (4H, AB quartet aromatic C—H).

EXAMPLE 121

Preparation of Methyl-5-bromo-2-(4-hydroxyphenyl)thiazol-4-yl acetic ester. (Compound No. 174 in Table I)

This compound was prepared by a method as described in Example 83 followed by esterification in Example 2.

$^1$H NMR (CDCl$_3$+d$_6$ DMSO) 3.7 (3H, s, CO$_2$CH$_3$), 3.8 (2H, s, CH$_2$CO), 7.3 (4H, AB quartet, aromatic C—H).

EXAMPLE 122

Preparation of Compound No. 176 in Table I

A mixture of 4-chlorothiobenzamide (8.6 g, 54.7 mmol) dimethyl-3-oxo-2-chloroglutarate (Bader, 1 equiv, 10.2 g) and dry methanol (100 ml) were heated under reflux for 8 hours. The reaction mixture was cooled to room temperature and the product (compound number 175) (8.6 g) was obtained on filtration.

$^1$H NMR (CDCl$_3$) 3.70 (3H, s, CO$_2$CH$_3$), 3.9 (3H, s, CO$_2$CH$_3$), 4.3 (2H, s, CHCO), and 7.7 (4H, AB quartet, aromatic C—H).

Compound No. 175 (Example 122) (2.0 g) was base hydrolysed in the usual way to give the desired product (1.3 g).

$^1$H NMR (d$_6$ DMSO) 4.25 (2H, s, CH$_2$CO), and 7.7 (4H, AB quartet, aromatic C—H).

EXAMPLE 124

Preparation of 5-Hydroxy-2-(4-chlorophenyl)thiazol-4-ylacetic acid. (Compound No. 177 in Table I)

A mixture of methyl-4-chlorothiobenzoate (2.11 g, 11.3 mmol), aspartic acid (2.7 g, 2.02 mmol), aq NaOH (3N, 8.8 ml), and Et$_2$O (8 ml) were vigourously stirred at room temperature for 3 days. The aq. layer was separated, acidified (dil.HCl), and extracted with Et$_2$O (2×25 ml). The combined ether extracts were dried (MgSO$_4$), filtered, and concentrated under reduced pressure to yield N-p-chlorothiobenzoylaspartic acid (0.23 g).

$^1$H NMR (CDCl$_3$+d$_6$ DMSO) 3.4 (2H, dq, CH$_2$CO$_2$H), 5.7 (1H, m, HN—CH), 7.6 (4H, ABq, aromatic C—H), 7.8 (2H, bs, 2×CO$_2$H), and 8.4 (1H, d, NH—CH).

This was dissolved in trifluoroacetic acid (1 ml) and stirred at room temperature for 12 hour, and concentrated under reduced pressure to give the desired product (0.15 g).

$^1$H NMR (d$_6$ DMSO) 3.5 (2H, s, CH$_2$CO$_2$H), and 7.6 (4H, AB quartet, aromatic C—H).

Note: NMR in CDCl$_3$ indicates presence of 5-(4H)-one-2-(4-chlorophenyl) thiazol-4-yl acetic acid tautomer.

EXAMPLE 125

Preparation of Methyl-2-[5-methyl-2-(4-chlorophenyl)thiazol-4-yl]propionate. (Compound No. 178 in Table I)

A mixture of methyl-(4-bromo-2-methyl-3-oxo) pentanoate (1.0 g, 4.5 mmol), 4-chlorothiobenzamide (0.7 g, 4.5 mmol) and ethanol were heated under reflux for 17 hours. The reaction mixture was cooled and concentrated under reduced pressure. The residue was dissolved in CHCl$_3$, and washed with NaHCO$_3$ solution, water, dried (MgSO$_4$) filtered and concentrated under reduced pressure to yield the product (0.34 g).

$^1$H NMR (CDCl$_3$) 1.55 (3H, d, CH$_3$CH), 2.45 (3H, s, thiazole CH$_3$), 3.7 (3H, s, CO$_2$CH$_3$), 3.95 (1H, q, CH$_3$CH), and 7.6 and (4H, AB quartet, aromatic C—H).

EXAMPLE 126

Preparation of Methyl-2-[5-bromomethyl-2-(4-chlorophenyl)thiazol-4-yl]propionate. (Compound No. 179 in Table I)

A mixture of methyl-2-(5-methyl-2-(4-chlorophenyl)-thiazol-4-yl)propionate (Compound No. 178) (0.5 g, 1.7 mmol), NBS (0.33 g 1.87 mmol), benzoyl perodide (cat.), were irradiated (UV) for 2 hours. The reaction mixture was cooled, filtered, and the filtrate concentrated under reduced pressure. The residue on trituration with hexane gave the product (0.45 g).

$^1$H NMR (CDCl$_3$) 1.65 (3H, d, CH$_3$CH), 3.7 (3H, s, CO$_2$CH$_3$), 4.0 (1H, q, CH$_3$CH), 4.8 (2H, AB quartet, CH$_2$Br), and 7.65 (4H, AB quartet, aromatic C—H).

EXAMPLE 127

Preparation of compound No. 133 in Table 1

A mixture of methyl-5-bromo-2-(4-chlorophenyl)-thiazol-4-yl acetic ester, (1.0 g, 3.0 mmol), Lawessons reagent (2.5 g, 6.2 mmol) and xylene (10 ml) were heated under reflux for 6 hours. The reaction mixture was cooled, filtered and 5 g of silica added to the filtrate. The mixture was concentrated under reduced pressure, extracted with CHCl$_3$. The combined CHCl$_3$ extracts were dried, filtered and concentrated under reduced pressure. The product was purified by chromatography (eluted with 50% Et$_2$O/hexane) to give the desired compound.

$^1$H NMR (CDCl$_3$) 4.10 (3H, s,

4.25 (2H, s, CH$_2$CO), and 7.6 (4H, AB quartet, aromatic C—H).

BIOLOGICAL DATA

The herbicidal activity of the compounds of formula (I) was tested as follows:

The compound in the appropriate concentration was incorporated into a 4% emulsion of methyl cyclohexanone and a 0.4% blend of 3.6 parts Tween 20 and 1 part Span 80. Tween 20 is a Trade Mark for a surface active agent comprising a condensate of 20 molar proportions of ethylene oxide with sorbitan laurate. Span 80 is a Trade Mark for a surface-active agent comprising sorbitan monolaurate. Formulation was effected by dissolving the compound in the requisite amount of solvent/surfactant blend. If necessary glass beads were added, the total liquid volume adjusted to 5 ml with water and the mixture shaken to effect complete dissolution of the compound. The formulation so prepared, after removal of beads where necessary, was then diluted to final spray volume (45 ml) with water.

The spray compositions so prepared were sprayed onto young pot plants (post-emergence test) at a rate equivalent to 1000 liters per hectare. Damage to plants was assessed 13 days after spraying by comparison with untreated plants, on a scale of 0 to 5 where 0 is 0-10% damage, 1 is 11 to 25% damage, 2 is 65-50% damage, 3 is 51-80% damage, 4 is 81-95% damage and 5 is 96-100% damage.

In a test carried out to detect pre-emergence herbicidal activity, seeds of the test species were placed on the surface of plastic trays of compost and sprayed with the compositions at the rate of 1000 liters per hectare. The seeds were then covered with further compost. 20 Days after spraying, the seedlings in the sprayed plastic trays, are compared to seedlings in untreated control trays, the damage being assessed on same scale of 0-5.

The results of the tests are given in Table III below.

TABLE III

| COMPOUND NO. | RATE OF APPLICATION kg/ha | PRE- OR POST EMERGENCE APPLICATION | TEST PLANTS (SEE TABLE IV) |
|---|---|---|---|
| | | | Sb Rp Ct Sy Mz Ww Rc Bd Ip Am Pi Ca Ga Xa Ab Co Av Dg Al St Ec Sh Ag Cn |
| 4 | 4 | Pre | |
| | | Post | |
| 17 | 4 | Pre | |
| | | Post | |
| 19 | 4 | Pre | |
| | | Post | |
| 20 | 4 | Pre | |
| | | Post | |
| 24 | 5 | Pre | |
| | | Post | |
| 57 | 4 | Pre | |
| | | Post | |
| 61 | 4 | Pre | |
| | | Post | |
| 63 | 4 | Pre | |
| | | Post | |
| 183 | 4 | Pre | |
| | | Post | |
| 186 | 4 | Pre | |
| | | Post | |
| 187 | 4 | Pre | |
| 193 | 4 | Pre | |
| 194 | 4 | Pre | |
| 195 | 4 | Pre | |
| 68 | 4 | Pre | |
| | | Post | |
| 70 | 4 | Pre | |
| | | Post | |
| 71 | 4 | Pre | |
| | | Post | |
| 72 | 4 | Pre | |
| | | Post | |
| 76 | 4 | Pre | |
| 178 | 3.75 | Pre | |
| | | Post | |
| 123 | 4 | Pre | |
| | | Post | |
| 122 | 3 | Pre | |
| | | Post | |

TABLE IV

Abbreviations Used for Test Plants

Sb—Sugar Beet
Rp—Rape
Ct—Cotton
Sy—Soybean
Mz—Maize
Ww—Winter wheat
Rc—Rice
Bd—*Bidens pilosa*
Ip—*Ipomoae purpurea*
Am—*Amaranthus retroflexus*
Pi—*Polygonum aviculare*
Ca—*Chenopodium album*
Ga—*Galium aparine*
Xa—*Xanthium spinosum*
Xs—*Xanthium strumarium*
Ab—*Abutilon theophrasti*
Co—*Cassia obtusifolia*
Av—*Avena fatua*
Dg—*Digitaria sanquinalis*
Al—*Alopercurus myosuroides*
St—*Setaria viridis*
Ec—*Echinchloa crus-galli*
Sh—*Sorghum halepense*
Ag—*Agropyron repens*
Cn—*Cyperus rotundus*

The herbicidal activity of some of the compounds was tested by an alternative method as follows: Each compound in the appropriate concentration was incorporated into a 4% emulsion of methylcylohexanone and 0.4% blend of 3.6 parts Tween 20 and 1 part Span 80. Tween 20 is a Trade Mark for a surface active agent comprising a condensate of 20 molar proportions of ethylene oxide with sorbitan laurate. Span 80 is a Trade Mark for a surface-active agent comprising sorbitan monolaurate. Formulation was effected by dissolving the compound in the requisite amount of solvent/surfactant blend. If necessary, glass beads were added, the total liquid volume adjusted to 5 ml with water, and the mixture shaken to effect complete dissolution of the compound. The formulation so prepared, after removal of beads where necessary, was then diluted to final spray volume (45 ml) with water.

The spray compositions so prepared were sprayed onto young pot plants (post-emergence test) at a rate equivalent to 1000 liters per hectare. Damage to plants was assessed 13 days after spraying by comparison with untreated plants, on a scale of 0 to 9 where 0 is 0% damage, 1 is 1–5% damage, 2 is 6–15% damage, 3 is 16–25% damage, 4 is 26–35% damage, 5 is 36–59% damage, 6 is 60–69% damage, 7 is 70–79% damage, 8 is 80–89% damage and 9 is 90–100% damage.

In a test carried out to detect pre-emergence herbicidal activity, crop seeds were sown at 2 cm depth (i.e. Sb, Ct, Rp, Ww, Mz, Rc, Sy) and weed seeds at 1 cm depth beneath compost and sprayed with the compositions at the rate of 1000 liters per hectate. 20 days after spraying, the seedlings in the sprayed plastic trays were compared with the seedlings in unsprayed control trays, the damage being assessed on the same scale of 0–9.

The results of the tests are given in Table V below.

TABLE V

| COMPOUND NO. | RATE OF APPLICATION kg/ha | PRE- OR POST EMERGENCE APPLICATION | Sb | Rp | Cl | Sy | Mz | Rc | Ww | Pi | Ca | Gn | Am | Bd | Eh | Ip | Ab | Xa | Xs | Av | Al | Ag | Sh | St | Dg | Ec | Ce |
|---|---|---|---|---|---|---|---|---|---|---|---|---|---|---|---|---|---|---|---|---|---|---|---|---|---|---|---|
| 81 | 4 | Pre | 1 | 0 | 0 | 0 | 0 | 2 | 0 | — | 3 | — | 0 | 0 | 0 | 0 | 0 | — | — | 0 | 0 | — | 0 | 0 | 2 | 0 | 0 |
|  |  | Post | 7 | 7 | 7 | 9 | 4 | 0 | 0 | 8 | 6 | 7 | 8 | 7 | 4 | 7 | 7 | — | 8 | 0 | 0 | 2 | 2 | 4 | 2 | 2 | 0 |
| 90 | 4 | Post | 5 | 5 | 6 | 9 | 0 | 0 | 0 | — | 8 | 8 | 7 | 6 | 3 | 2 | 7 | — | 7 | 0 | 0 | 5 | — | 0 | 0 | 0 | 0 |
| 94 | 4 | Pre | 1 | 0 | 0 | 1 | 6 | 0 | 0 | — | 0 | — | 0 | 0 | 0 | 0 | 0 | — | — | 0 | 0 | — | 1 | 0 | 0 | 0 | — |
|  |  | Post | 6 | 6 | 8 | 8 | 6 | 0 | 0 | 5 | 6 | — | 8 | 8 | 5 | 2 | 6 | — | 7 | 0 | 0 | 3 | 2 | 0 | 3 | 0 | 0 |
| 71 | 4 | Pre | 0 | 0 | 0 | 0 | 0 | 0 | 0 | — | 0 | — | 0 | 0 | 0 | 0 | 0 | — | — | 0 | 0 | — | 0 | 0 | 0 | 0 | 0 |
|  |  | Post | 5 | 8 | 9 | 9 | 6 | 0 | 3 | 7 | 8 | 8 | 9 | 8 | 4 | 6 | 7 | — | 7 | 0 | 0 | 4 | 4 | 5 | 5 | 4 | 0 |
| 107 | 4 | Post | 7 | 8 | 8 | 8 | 8 | 0 | 0 | 7 | 9 | 8 | 9 | 0 | 5 | 5 | 7 | — | 8 | 0 | 0 | 5 | 4 | 2 | 8 | 0 | 0 |
| 100 | 4 | Post | 6 | 8 | 8 | 8 | 6 | 1 | 2 | 7 | 8 | 8 | 9 | 7 | 5 | 5 | 7 | — | 8 | 2 | 0 | 6 | 4 | 3 | 3 | 6 | 0 |
| 114 | 4 | Post | 5 | 8 | 8 | 9 | 6 | 0 | 0 | 8 | 8 | 8 | 9 | 7 | 5 | 8 | 7 | — | 7 | 0 | 0 | 5 | 4 | 4 | 6 | 5 | 0 |
| 115 | 4 | Post | 5 | 9 | 8 | 9 | 3 | 2 | 2 | 5 | 6 | 8 | 9 | 7 | 5 | 5 | 7 | — | 8 | 0 | 0 | 2 | 4 | 4 | 6 | 0 | 0 |
| 109 | 4 | Post | 6 | 7 | 8 | 9 | — | — | 0 | 6 | 7 | 8 | 6 | 7 | 4 | 3 | 6 | — | 7 | 0 | 0 | 0 | 5 | 4 | 6 | 6 | 5 |
| 124 | 2.2 | Pre | 0 | 0 | 0 | 7 | 0 | 1 | 2 | 5 | 7 | 9 | 9 | 8 | 4 | 0 | 6 | 9 | 8 | 0 | 2 | — | 4 | 0 | — | 0 | 5 |
|  |  | Post | 1 | 2 | 3 | 7 | 0 | 1 | 7 | 7 | 5 | 5 | 0 | 0 | 3 | — | 0 | 0 | — | 0 | 2 | 4 | 5 | 0 | — | 0 | 0 |
| 127 | 4 | Pre | 0 | 0 | 0 | 0 | 2 | 5 | 2 | 2 | 0 | 0 | 5 | 5 | 0 | 0 | 9 | 0 | 9 | 0 | 0 | — | 0 | 0 | 0 | 0 | 0 |
|  |  | Post | 0 | 7 | 4 | 2 | 0 | 3 | 0 | 5 | 7 | 9 | 9 | — | 3 | 0 | 3 | — | 3 | 0 | 0 | 0 | 0 | 0 | 0 | 0 | 3 |
| 128 | 4 | Pre | 0 | 0 | 0 | 3 | 2 | 0 | 5 | 4 | 2 | 3 | 0 | — | 0 | 0 | 4 | 0 | 5 | 0 | 0 | — | 0 | 0 | 0 | 0 | 0 |
|  |  | Post | 0 | 7 | 4 | 9 | 0 | 0 | 5 | 0 | 7 | 7 | 7 | 5 | 3 | 0 | 7 | — | 8 | 0 | 2 | — | 3 | 0 | 2 | — | 0 |
| 132 | 1 | Pre | 0 | 7 | 5 | 9 | 3 | 4 | 4 | 2 | 8 | 7 | 7 | 9 | 0 | 6 | 7 | — | 7 | 2 | 2 | 3 | 3 | 2 | 5 | 8 | 2 |
| 147 | 2.4 | Post | 6 | 8 | 6 | 9 | 4 | 3 | 4 | 6 | 7 | 7 | 7 | 8 | 6 | 7 | 7 | — | 8 | 3 | 2 | 2 | 0 | 4 | 3 | 4 | 0 |
| 148 | 2.4 | Post | 6 | 5 | 7 | 7 | 5 | 2 | 5 | 7 | 7 | 7 | 7 | 7 | 6 | 7 | 8 | — | 6 | 3 | 2 | 2 | 2 | 4 | 5 | 5 | 0 |
| 149 | 2.4 | Post | 5 | 4 | 4 | 8 | 4 | 2 | 3 | 6 | 5 | 6 | 4 | 8 | 6 | 5 | 6 | — | 6 | 2 | 3 | 3 | 2 | 2 | 4 | 4 | 0 |
| 150 | 2.4 | Post | 5 | 4 | 4 | 9 | 4 | — | 4 | 3 | 5 | 5 | 0 | 6 | 3 | 5 | 6 | — | — | — | 0 | 0 | 0 | 0 | 2 | 3 | 0 |
| 162 | 4 | Pre | 0 | 0 | 0 | 0 | 0 | 0 | 0 | 0 | 0 | — | 0 | 0 | 0 | 0 | 0 | — | 1 | 0 | 0 | 0 | — | 0 | 0 | 0 | 0 |
|  |  | Post | 0 | 0 | 0 | 0 | 0 | 0 | 3 | 0 | 0 | — | 0 | 0 | 0 | 0 | 2 | — | — | 0 | 5 | — | 0 | 0 | 0 | 0 | 0 |
| 163 | 4 | Pre | 0 | 2 | 2 | 2 | 2 | 5 | 0 | 0 | 2 | — | 2 | 2 | 0 | 0 | 5 | — | — | 0 | 0 | — | 0 | 0 | 0 | 0 | 3 |
|  |  | Post | 0 | 6 | 0 | 0 | 2 | 0 | 3 | 0 | 2 | 0 | 2 | 2 | 0 | 0 | 0 | — | 0 | 2 | 0 | — | 0 | 0 | 0 | 6 | 0 |
| 164 | 4 | Post | 2 | 6 | 0 | 0 | 2 | 0 | 0 | 0 | 2 | 4 | 2 | 0 | 0 | 0 | 0 | — | 0 | 0 | 0 | — | 0 | 0 | 0 | 6 | 0 |
| 168 | 4 | Post | 2 | 0 | 4 | 9 | 0 | 0 | 0 | 2 | 3 | — | 3 | 4 | 2 | 3 | 7 | — | — | 0 | 0 | 0 | 0 | 0 | 0 | 0 | 0 |

TABLE VI

Abbreviations Used for Test Plants in Table V

Sb—Sugar beet
Rp—Rape
Ct—Cotton
Sy—Soybean
Mz—Maize
Rc—Rice
Ww—Winter wheat
Bd—*Bidens pilosa*
Ip—*Ipomoea lacunosa* (pre-emergence),
*Ipomoea hederacea* (post emergence)
Am—*Amaranthus retroflexus*
Pi—*Polygonum aviculare*
Ca—*Chenopodium album*
Ga—*Galium aparine*
Xa—*Xanthium spinosum*
Xs—*Xanthium strumarium*
Ab—*Abutilon theophrasti*
Eh—*Euphorbia heterophylla*
Av—*Avena fatua*
Dg—*Digitaria sanquinalis*
Al—*Alopecuris myosuroides*
St—*Setaria viridis*
Ec—*Echinochloa crus-galli*
Sh—*Sorghum halepense*
Ag—*Agropyron repens*
Ce—*Cyperus esculentes*

We claim:

1. A compound of formula (II)

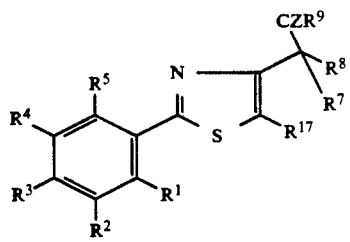

(II)

wherein $R^1$, $R^2$, $R^3$, $R^4$, and $R^5$ are independently selected from hydrogen, hydroxy, $C_1$–$C_{10}$ alkyl, $C_1$–$C_{10}$ alkoxy, ($C_1$–$C_{10}$ alkyl)carbonyl, halogen, cyano, nitro, halo-($C_1$–$C_{10}$)alkyl and halo-($C_1$–$C_{10}$)alkoxy; $R^7$ is hydrogen, $C_1$–$C_3$ alkyl, halo-($C_1$–$C_{10}$)alkyl, $C(O)_m R^{10}$ or halogen; wherein $R^{10}$ is hydrogen, $C_1$–$C_{10}$ alkyl, $C_2$–$C_{10}$ alkenyl, $C_2$–$C_{10}$ alkynyl or phenyl, any of which may be optionally substituted and m is 1 or 2 $R^8$ is hydrogen, $C_1$–$C_3$ alkyl or halogen or the group $R_7$ and $R^8$ together form an oxo group; and the group $CZR^9$ is carboxy or an ester thereof having the formula $COOR^{15}$ wherein $R^{15}$ is a substituted for alkyl, alkenyl, alkynyl or phenyl groups as defined for $R_{10}$ and $R_{15}$ or substituted $C_1$–$C_{10}$ alkyl, $C_2$–$C_{10}$ alkenyl, $C_2$–$C_{10}$ alkynyl or phenyl group and the substituents are one or more groups selected from halogen; hydroxy; $C_1$–$C_6$ alkoxy; $C_{(1-6)}$alkoxy$C_{(1-6)}$alkoxy; $C_1$–$C_6$ alkoxy substituted by phenyl or naphthyl; nitro; $C_3$–$C_{10}$ cycloalkyl; a heterocyclic group having a ring of from 3 to 10 atoms containing at least one atom selected from oxygen, nitrogen or sulphur, optionally substituted by oxo; cyano; phenyl optionally substituted by nitro, halo, $C_1$–$C_6$ alkoxy or carboxy or salts or $C_1$–$C_6$alkyl esters thereof, or $C_1$–$C_{10}$ alkylsilyl; or $R^9$ is a group $SR^{10}$ or $NR^{11}R^{12}$ wherein $R^{11}$ is hydrogen or $C_1$–$C_{10}$ alkyl and $R^{12}$ is hydrogen, optionally substituted $C_1$–$C_{10}$ alkyl optionally substituted by carboxy or by a $C_1$–$C_3$ alkyl carboxylic ester, $S(O)_n R^{10}$, wherein n is 0, 1 or 2, or $R^9$ is a group —$NR^{11}NR^{13}R^{14}$ wherein $R^{11}$, $R^{13}$ and $R^{14}$ are independently selected from hydrogen or $C_1$–$C_{10}$ alkyl; or $R^9$ is a group —$NR^{11}+NR^{13}R^{14}R^{20}X^-$ wherein $R^{11}$, $R^{13}$ and $R^{14}$ and $R^{20}$ are each hydrogen or $C_1$–$C_{10}$ alkyl, and $X^-$ is an agriculturally acceptable anion; Z is oxygen or sulphur and $R^{17}$ is halogen, cyano, nitro, hydroxy, amino or mono or di-$C_1$–$C_{10}$) alkylamine.

2. A compound according to claim 1 in which $R^1$, $R^2$, $R^4$ and $R^5$ is each hydrogen, $R^3$ is chlorine and $R^{17}$ is bromine.

3. A compound according to claim 2 in which $R^7$ and $R^8$ are each hydrogen, Z is oxygen, $R^9$ is $SR^{10}$ and $R^{10}$ is $C_1$–$C_{10}$ alkyl.

4. A compound according to claim 2 in which $R^7$ and $R^8$ are each hydrogen, and the group $CZR^9$ is a $C_1$–$C_{10}$ alkyl, a benzyl, a phenylethyl, or a halobenzyl carboxylic ester.

5. A compound according to claim 2 in which the group $CZR^9$ has the formula $CO_2R^{15}$ in which $R^{15}$ is a substituted or unsubstituted $C_1$–$C_{10}$ alkyl, $C_2$–$C_{10}$ alkenyl, $C_2$–$C_{10}$ alkynyl or phenyl group.

6. A compound according to claim 4 in which the group $CZR^9$ is $COO(CH_2)_2CH_3$.

7. A compound according to claim 4 in which the group $CZR^9$ is $COOCH_2CH_3$.

8. A compound according to claim 4 in which the group $CZR^9$ is $COOCH_2C_6H_5$.

* * * * *